US010234394B2

(12) United States Patent
Chou et al.

(10) Patent No.: US 10,234,394 B2
(45) Date of Patent: *Mar. 19, 2019

(54) METHOD FOR HIGHLY SENSITIVE DETECTION OF BIOMARKERS FOR DIAGNOSTICS

(71) Applicant: The Trustees of Princeton University, Princeton, NJ (US)

(72) Inventors: Stephen Y. Chou, Princeton, NJ (US); Liang-Cheng Zhou, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/668,750

(22) Filed: Mar. 25, 2015

(65) Prior Publication Data

US 2015/0338346 A1 Nov. 26, 2015

Related U.S. Application Data

(63) Continuation of application No. 13/838,600, filed on Mar. 15, 2013, which is a continuation-in-part of
(Continued)

(51) Int. Cl.
*B82Y 15/00* (2011.01)
*G01N 21/64* (2006.01)
*G01N 21/65* (2006.01)

(52) U.S. Cl.
CPC .......... *G01N 21/6486* (2013.01); *B82Y 15/00* (2013.01); *G01N 21/648* (2013.01);
(Continued)

(58) Field of Classification Search
CPC .. G01N 21/554; G01N 21/658; G01N 33/587; G01N 21/6486; G01N 21/6248;
(Continued)

(56) References Cited

U.S. PATENT DOCUMENTS 5,552,272 A 9/1996 Bogart
5,866,430 A 2/1999 Grow
(Continued)

FOREIGN PATENT DOCUMENTS

CN 101553724 10/2009
CN 101606057 12/2009
(Continued)

OTHER PUBLICATIONS

Hu, et al., "Effects of nanodots on surface plasmons and electric field enhancement in nano-pillar antenna array", Quantum Electronics and Laser Science Conference, San Jose, California, US, May 16-21, 2010.
(Continued)

*Primary Examiner* — Dominic J Bologna
(74) *Attorney, Agent, or Firm* — James S. Keddie; Bozicevic, Field & Francis, LLP

(57) ABSTRACT

This disclosure provides, among other things, a nanosensor comprising a substrate and one or a plurality of pillars extending from a surface of the substrate, where the pillars comprise a metallic dot structure, a metal disc, and a metallic back plane. The nanosensor comprises a molecular adhesion layer that covers at least a part of the metallic dot structure, the metal disc, and/or the metallic back plane and a capture agent bound to the molecular adhesion layer. The nanosensor amplifies a light signal from an analyte, when the analyte is specifically bound to the capture agent.

30 Claims, 19 Drawing Sheets

Specification includes a Sequence Listing.

Related U.S. Application Data application No. 13/699,270, filed as application No. PCT/US2011/037455 on May 20, 2011, now Pat. No. 9,182,338.

(60) Provisional application No. 61/622,226, filed on Apr. 10, 2012, provisional application No. 61/347,178, filed on May 21, 2010.

(52) U.S. Cl.
CPC ....... *G01N 21/6428* (2013.01); *G01N 21/658* (2013.01); *G01N 2021/6439* (2013.01); *G01N 2201/06113* (2013.01)

(58) Field of Classification Search
CPC ......... G01N 21/648; G01N 2021/6439; G01N 2201/06113; B82Y 33/587; B82Y 15/00
See application file for complete search history.

(56) References Cited

U.S. PATENT DOCUMENTS

| | | | |
|---|---|---|---|
| 6,127,120 A * | 10/2000 | Graham | C12Q 1/6816 435/6.14 |
| 6,743,581 B1 | 6/2004 | Vo-Dinh | |
| 7,153,682 B2 | 12/2006 | Charych et al. | |
| 7,245,370 B2 | 7/2007 | Bratkovski et al. | |
| 7,388,661 B2 | 6/2008 | Li et al. | |
| 7,426,025 B2 | 9/2008 | Wang | |
| 7,500,953 B2 | 3/2009 | Oraevsky et al. | |
| 7,586,601 B2 | 9/2009 | Ebstein | |
| 7,713,849 B2 | 5/2010 | Habib et al. | |
| 7,714,317 B2 | 5/2010 | Sutter et al. | |
| 7,851,172 B2 | 12/2010 | Lovell et al. | |
| 7,892,489 B2 | 2/2011 | Wang et al. | |
| 9,013,690 B1 * | 4/2015 | Chou et al. | 356/317 |
| 2002/0109110 A1 | 8/2002 | Some et al. | |
| 2003/0026900 A1 | 2/2003 | Weimer | |
| 2004/0156108 A1 | 8/2004 | Chou et al. | |
| 2005/0034729 A1 | 2/2005 | Dombrowski | |
| 2005/0084912 A1 * | 4/2005 | Poponin | G01N 21/658 435/7.1 |
| 2006/0038990 A1 * | 2/2006 | Habib | G01N 21/658 356/301 |
| 2006/0146323 A1 * | 7/2006 | Bratkovski | G01N 21/658 356/301 |
| 2006/0252065 A1 * | 11/2006 | Zhao | B82Y 5/00 356/301 |
| 2007/0153267 A1 | 7/2007 | Wang et al. | |
| 2007/0155021 A1 | 7/2007 | Zhang et al. | |
| 2008/0024776 A1 * | 1/2008 | Bratkovski | G01N 21/658 356/301 |
| 2008/0094621 A1 | 4/2008 | Li et al. | |
| 2008/0145964 A1 | 6/2008 | Linden | |
| 2009/0097022 A1 | 4/2009 | Shen et al. | |
| 2009/0149344 A1 | 6/2009 | Zhao et al. | |
| 2009/0213369 A1 | 8/2009 | Lee et al. | |
| 2009/0214392 A1 * | 8/2009 | Kameoka | B01L 3/502761 356/301 |
| 2009/0263485 A1 * | 10/2009 | Li | G01N 33/587 424/489 |
| 2010/0078855 A1 | 1/2010 | Chou et al. | |
| 2010/0032321 A1 | 2/2010 | Kim et al. | |
| 2010/0126882 A1 | 5/2010 | Kim et al. | |
| 2011/0058164 A1 * | 3/2011 | Zhang | B82Y 15/00 356/301 |
| 2011/0128536 A1 | 6/2011 | Bond et al. | |

FOREIGN PATENT DOCUMENTS

| | | |
|---|---|---|
| JP | 2003510607 | 3/2003 |
| JP | 2007319988 | 6/2006 |
| JP | 2007240361 | 9/2007 |
| JP | 2011-506916 | 3/2011 |
| JP | 2011252928 | 12/2011 |
| JP | 2012063294 | 3/2012 |
| RU | 2426193 | 8/2011 |
| WO | WO 2010/056258 | 5/2010 |
| WO | WO2011016057 | 9/2011 |
| WO | WO2012024006 | 2/2012 |
| WO | WO2014055559 | 4/2014 |

OTHER PUBLICATIONS

Li, et al. "Three-dimensional cavity nanoantenna coupled plasmonic nanodots for ultrahigh and uniform surface-enhanced Raman scattering over large area", Feb. 2011, Optics Express, vol. 19, No. 5, pp. 3925-3936.

Love, et al. "Self-Assembled Monolayers of Thiolates on Metals as a Form of Nanotechnology", Chem. Rev. 2005, 105, pp. 1103-1169.

Zhou, et al., "Enhancement of Immunoassay's Fluorescence and Detection Sensitivity Using Three-Dimensional Plasmonic Nano-Antenna-Dots Array", Apr. 2012, ACS Publications, vol. 84, pp. 4489-4495.

Zhang, et al., "Giant and uniform fluorescence enhancement over large areas using plasmonic nanodots in 3D resonant cavity nanoantenna by nanoimprinting", May 2012, Nanotechnology, vol. 23, pp. 1-9.

Zin, et. al. "Surface-plasmon-enhanced fluorescence from periodic quantum dot arrays through distance control using biomolecular linkers", Nanotechnology, 2009, 20(1):015305, pp. 1-7.

Su, et. al, "Interparticle Coupling Effects on Plasmon Resonances of Nanogold Particles", Nano Letters, 2003, 3 (8), pp. 1087-1090.

* cited by examiner

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 1
gaagaagata gacttacatg                                              20

<210> SEQ ID NO 2
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 2
tttggcttgt ggtagttaga                                              20

<210> SEQ ID NO 3
<211> LENGTH: 40
<212> TYPE: DNA
<213> ORGANISM: artificial sequence
<220> FEATURE:
<223> OTHER INFORMATION: synthetic polynucleotide

<400> SEQUENCE: 3
accgaacacc atcaatctct tctatctgaa tgtactttt                          40

US 10,234,394 B2

METHOD FOR HIGHLY SENSITIVE DETECTION OF BIOMARKERS FOR DIAGNOSTICS

CROSS-REFERENCING

This application claims the benefit of U.S. provisional application Ser. No. 61/622,226 filed on Apr. 10, 2012, and is a continuation-in-part of U.S. patent application Ser. No. 13/699,270, filed on Jan. 24, 2013, which application is a § 371 filing of US2011/037455, filed May 20, 2011 and claims the benefit of U.S. provisional application Ser. No. 61/347,178, filed on May 21, 2010, which applications are incorporated by reference herein for all purposes.

STATEMENT REGARDING FEDERALLY SPONSORED RESEARCH

This invention was made with United States government support under Grant No. FA9550-08-1-0222 awarded by the Defense Advanced Research Project Agency (DARPA) The United States government has certain rights in this invention.

BACKGROUND

There is a great need to enhance a luminescence signal (e.g. a fluorescence signal) and detection sensitivity of biological and chemical assays. The application is related to the micro/nanostructures and molecular layers and methods for achieving an enhancement (namely amplification of luminescence and improvement of detection sensitivity), their fabrication and applications.

SUMMARY

This disclosure provides, among other things, a nanosensor comprising a substrate and one or a plurality of pillars extending from a surface of the substrate, with a metallic dot structure on pillar's sidewall, a metal disc on top of the pillar, and a metallic back plane covering a significant area near the foot of the pillar. The nanosensor further comprises a molecular adhesion layer that covers at least a part of the metallic dot structure, and/or the metal disc, and/or the metallic back plane and that binds a capture agent. The nanosensor is coated with capture agent that specifically captures targeted analytes (e.g. molecules, which can be proteins or nucleic acids). The analytes can be optically labeled directly or indirectly. In indirect labeling, a secondary capture agent with an optical label (i.e. a labeled detection agent) is used to bind and hence identify the presence of the captured analyte. The nanosensor amplifies a light signal from a the analyte, when the analyte is bound to the capture agent.

BRIEF DESCRIPTION OF THE DRAWINGS

The skilled artisan will understand that the drawings, described below, are for illustration purposes only. The drawings are not intended to limit the scope of the present teachings in any way. Some of the drawings are not in scale.

Corresponding reference numerals indicate corresponding parts throughout the several figures of the drawings. It is to be understood that the drawings are for illustrating the concepts set forth in the present disclosure and are not to scale.

Figure 1:
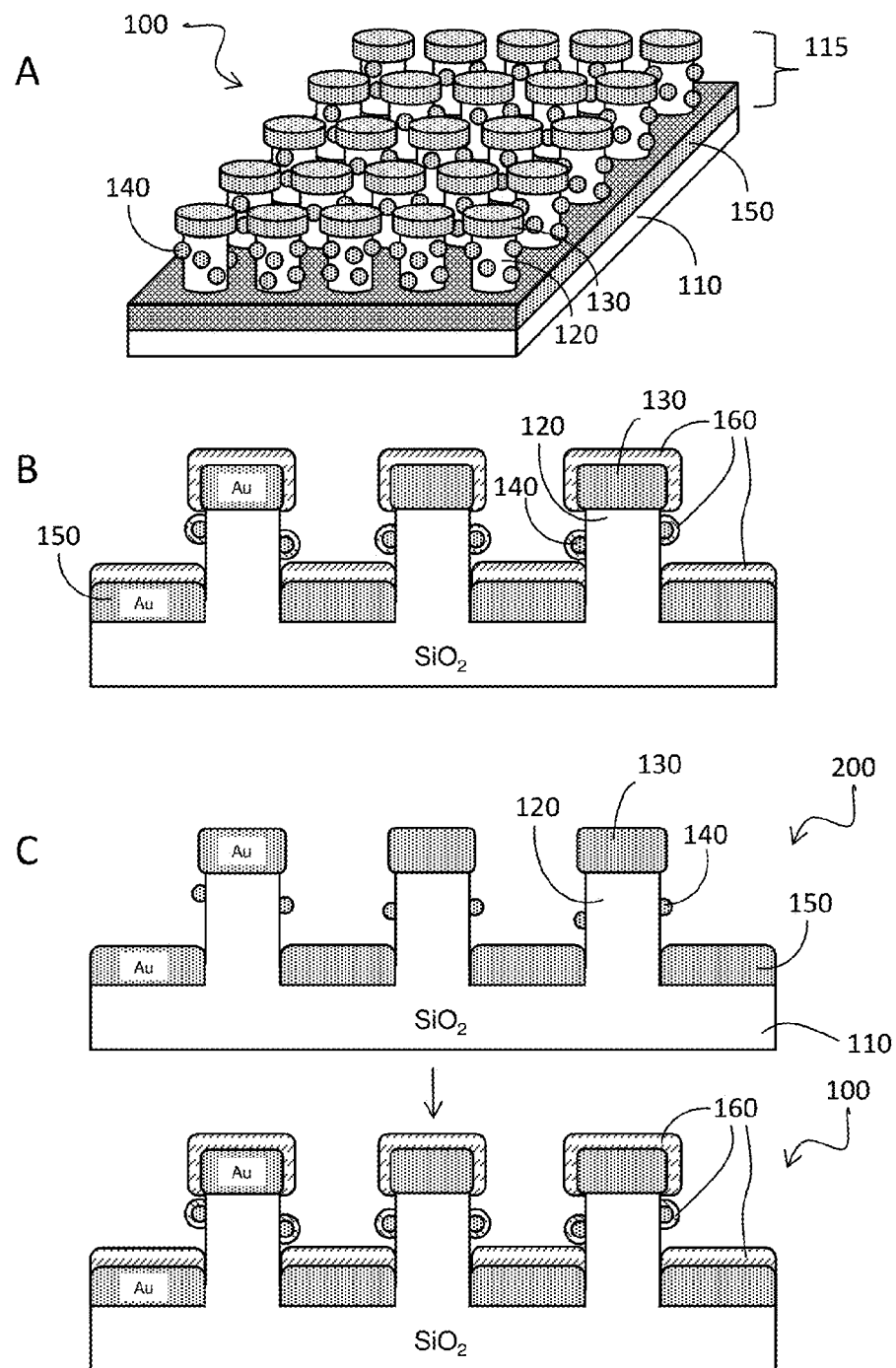
FIG. 1 panels A and B schematically illustrate some features of embodiment of a subject nanodevice. Panel C schematically illustrates one way in which a subject nanodevice can be manufactured.

Before any embodiments of the invention are explained in detail, it is to be understood that the invention is not limited in its application to the details of construction and the arrangement of components set forth in the following description or illustrated in the drawings.

Definitions

Before describing exemplary embodiments in greater detail, the following definitions are set forth to illustrate and define the meaning and scope of the terms used in the description.

The term "molecular adhesion layer" refers to a layer or multilayer of molecules of defined thickness that comprises an inner surface that is attached to the nanodevice and an outer (exterior) surface can be bound to capture agents.

The term "capture agent-reactive group" refers to a moiety of chemical function in a molecule that is reactive with capture agents, i.e., can react with a moiety (e.g., a hydroxyl, sulfhydryl, carboxy or amine group) in a capture agent to produce a stable strong, e.g., covalent bond.

The term "capture agent" as used herein refers to an agent that binds to a target analyte through an interaction that is sufficient to permit the agent to bind and concentrate the target molecule from a heterogeneous mixture of different molecules. The binding interaction is typically mediated by an affinity region of the capture agent. Typical capture agents include any moiety that can specifically bind to a target analyte. Certain capture agents specifically bind a target molecule with a dissociation constant ($K_D$) of less than about $10^{-6}$ M (e.g., less than about $10^{-7}$ M, less than about $10^{-8}$ M, less than about $10^{-9}$ M, less than about $10^{-10}$ M, less than about $10^{-11}$ M, less than about $10^{-12}$ M, to as low as $10^{-16}$ M) without significantly binding to other molecules. Exemplary capture agents include proteins (e.g., antibodies), and nucleic acids (e.g., oligonucleotides, DNA, RNA including aptamers).

The terms "specific binding" and "selective binding" refer to the ability of a capture agent to preferentially bind to a particular target molecule that is present in a heterogeneous mixture of different target molecule. A specific or selective binding interaction will discriminate between desirable (e.g., active) and undesirable (e.g., inactive) target molecules in a sample, typically more than about 10 to 100-fold or more (e.g., more than about 1000- or 10,000-fold).

The term "protein" refers to a polymeric form of amino acids of any length, i.e. greater than 2 amino acids, greater than about 5 amino acids, greater than about 10 amino acids, greater than about 20 amino acids, greater than about 50 amino acids, greater than about 100 amino acids, greater than about 200 amino acids, greater than about 500 amino acids, greater than about 1000 amino acids, greater than about 2000 amino acids, usually not greater than about 10,000 amino acids, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Also included by these terms are polypeptides that are post-translationally modified in a cell, e.g., glycosylated, cleaved, secreted, prenylated, carboxylated, phosphorylated, etc, and polypeptides with secondary or tertiary structure, and polypeptides that are strongly bound, e.g., covalently or non-covalently, to other moieties, e.g., other polypeptides, atoms, cofactors, etc.

The term "antibody" is intended to refer to an immunoglobulin or any fragment thereof, including single chain antibodies that are capable of antigen binding and phage display antibodies).

The term "nucleic acid" and "polynucleotide" are used interchangeably herein to describe a polymer of any length composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The term "complementary" as used herein refers to a nucleotide sequence that base-pairs by hydrogen bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. Typically, "complementary" refers to a nucleotide sequence that is fully complementary to a target of interest such that every nucleotide in the sequence is complementary to every nucleotide in the target nucleic acid in the corresponding positions. When a nucleotide sequence is not fully complementary (100% complementary) to a non-target sequence but still may base pair to the non-target sequence due to complementarity of certain stretches of nucleotide sequence to the non-target sequence, percent complementarily may be calculated to assess the possibility of a non-specific (off-target) binding. In general, a complementary of 50% or less does not lead to non-specific binding. In addition, a complementary of 70% or less may not lead to non-specific binding under stringent hybridization conditions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 200 nucleotides and up to 300 nucleotides in length, or longer, e.g., up to 500 nt in length or longer. Oligonucleotides may be synthetic and, in certain embodiments, are less than 300 nucleotides in length.

The term "attaching" as used herein refers to the strong, e.g, covalent or non-covalent, bond joining of one molecule to another.

The term "surface attached" as used herein refers to a molecule that is strongly attached to a surface.

The term "sample" as used herein relates to a material or mixture of materials containing one or more analytes of interest. In particular embodiments, the sample may be obtained from a biological sample such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In particular embodiments, a sample may be obtained from a subject, e.g., a human, and it may be processed prior to use in the subject assay. For example, prior to analysis, the protein/nucleic acid may be extracted from a tissue sample prior to use, methods for which are known. In particular embodiments, the sample may be a clinical sample, e.g., a sample collected from a patient.

The term "analyte" refers to a molecule (e.g., a protein, nucleic acid, or other molecule) that can bound by a capture agent and detected.

The term "assaying" refers to testing a sample to detect the presence and/or abundance of an analyte.

As used herein, the terms "determining," "measuring," and "assessing," and "assaying" are used interchangeably and include both quantitative and qualitative determinations.

As used herein, the term "light-emitting label" refers to a label that can emit light when under an external excitation. This can be luminescence. Fluorescent labels (which include dye molecules or quantum dots), and luminescent labels (e.g., electro- or chemi-luminescent labels) are types of light-emitting label. The external excitation is light (photons) for fluorescence, electrical current for electroluminescence and chemical reaction for chemi-luminscence. An external excitation can be a combination of the above.

The phrase "labeled analyte" refers to an analyte that is detectably labeled with a light emitting label such that the analyte can be detected by assessing the presence of the label. A labeled analyte may be labeled directly (i.e., the analyte itself may be directly conjugated to a label, e.g., via a strong bond, e.g., a covalent or non-covalent bond), or a labeled analyte may be labeled indirectly (i.e., the analyte is bound by a secondary capture agent that is directly labeled).

The term "hybridization" refers to the specific binding of a nucleic acid to a complementary nucleic acid via Watson-Crick base pairing. Accordingly, the term "in situ hybridization" refers to specific binding of a nucleic acid to a metaphase or interphase chromosome.

The terms "hybridizing" and "binding", with respect to nucleic acids, are used interchangeably.

The term "capture agent/analyte complex" is a complex that results from the specific binding of a capture agent with an analyte. A capture agent and an analyte for the capture agent will usually specifically bind to each other under "specific binding conditions" or "conditions suitable for specific binding", where such conditions are those conditions (in terms of salt concentration, pH, detergent, protein concentration, temperature, etc.) which allow for binding to occur between capture agents and analytes to bind in solution. Such conditions, particularly with respect to antibodies and their antigens and nucleic acid hybridization are well known in the art (see, e.g., Harlow and Lane (Antibodies: A Laboratory Manual Cold Spring Harbor Laboratory, Cold Spring Harbor, N.Y. (1989) and Ausubel, et al, Short Protocols in Molecular Biology, 5th ed., Wiley & Sons, 2002).

The term "specific binding conditions" as used herein refers to conditions that produce nucleic acid duplexes or protein/protein (e.g., antibody/antigen) complexes that contain pairs of molecules that specifically bind to one another, while, at the same time, disfavor to the formation of complexes between molecules that do not specifically bind to one another. Specific binding conditions are the summation or combination (totality) of both hybridization and wash conditions, and may include a wash and blocking steps, if necessary.

For nucleic acid hybridization, specific binding conditions can be achieved by incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C.

For binding of an antibody to an antigen, specific binding conditions can be achieved by blocking a substrate containing antibodies in blocking solution (e.g., PBS with 3% BSA or non-fat milk), followed by incubation with a sample containing analytes in diluted blocking buffer. After this incubation, the substrate is washed in washing solution (e.g. PBS+TWEEN 20) and incubated with a secondary capture antibody (detection antibody, which recognizes a second site in the antigen). The secondary capture antibody may conjugated with an optical detectable label, e.g., a fluorophore such as IRDye800CW, Alexa 790, Dylight 800. After another wash, the presence of the bound secondary capture antibody may be detected. One of skill in the art would be knowledgeable as to the parameters that can be modified to increase the signal detected and to reduce the background noise.

The term "a secondary capture agent" which can also be referred to as a "detection agent" refers a group of biomolecules or chemical compounds that have highly specific affinity to the antigen. The secondary capture agent can be strongly linked to an optical detectable label, e.g., enzyme, fluorescence label, or can itself be detected by another detection agent that is linked to an optical detectable label through bioconjugatio (Hermanson, "Bioconjugate Techniques" Academic Press, 2nd Ed., 2008).

The term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least 10-8M. A biotin affinity agent may also include a linker, e.g., -LC-biotin, -LC-LC-Biotin, -SLC-Biotin or -PEGn-Biotin where n is 3-12.

The term "streptavidin" refers to both streptavidin and avidin, as well as any variants thereof that bind to biotin with high affinity.

The term "marker" refers to an analyte whose presence or abundance in a biological sample is correlated with a disease or condition.

The term "bond" includes covalent and non-covalent bonds, including hydrogen bonds, ionic bonds and bonds produced by van der Waal forces.

The term "amplify" refers to an increase in the magnitude of a signal, e.g., at least a 10-fold increase, at least a 100-fold increase at least a 1,000-fold increase, at least a 10,000-fold increase, or at least a 100,000-fold increase in a signal.

Other specific binding conditions are known in the art and may also be employed herein.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, and reference to "a detection agent" includes a single detection agent and multiple detection agents.

DETAILED DESCRIPTION OF EXEMPLARY EMBODIMENTS

The following detailed description illustrates some embodiments of the invention by way of example and not by way of limitation.

With reference to FIGS. 1A and 1B, disclosed herein is nanodevice 100 comprising: (a) substrate 110; and (b) one or a plurality of pillars 115 extending from a surface of the substrate, wherein at least one of the pillars comprises a pillar body 120, metallic disc 130 on top of the pillar, metallic back plane 150 at the foot of the pillar, the metallic back plane covering a substantial portion of the substrate surface near the foot of the pillar; metallic dot structure 130 disposed on sidewall of the pillar and molecular adhesion layer 160 that covers at least a part of the metallic dot structure, and/or the metal disc, and/or the metallic back plane. The underlying structure in this device has been referred as "disk-coupled dots-on-pillar antenna array, (D2PA)" and examples are them have been described (see, e.g., Li et al Optics Express 2011 19, 3925-3936 and WO2012/024006, which are incorporated by reference).

The exterior surface of molecular adhesion layer 160 comprises a capture-agent-reactive group, i.e., a reactive group that can chemically react with capture agents, e.g., an amine-reactive group, a thiol-reactive group, a hydroxyl-reactive group, an imidazolyl-reactive group and a guanidinyl-reactive group. For illustrative purposes, the molecular adhesion layer 160 covers all of the exposed surface of metallic dot structure 160, metal disc 130, and metallic back plane 150. However, for practical purposes, adhesion layer 160 need only part of the exposed surface of metallic dot structure 160, metal disc 130, or metallic back plane 150. As shown, in certain cases, substrate 110 may be made of a dielectric (e.g., $SiO_2$) although other materials may be used, e.g., silicon, GaAs, polydimethylsiloxane (PDMS), poly(methyl methacrylate) (PMMA). Likewise, the metal may be gold, silver, platinum, palladium, lead, iron, titanium, nickel, copper, aluminum, alloy thereof, or combinations thereof, although other materials may be used, as long as the materials' plasma frequency is higher than that of the light signal and the light that is used to generate the light signal.

Nanodevice 100 is characterized in that it amplifies a light signal that is proximal to the exterior surface of the adhesion layer.

In some embodiments, the dimensions of one or more of the parts of the pillars or a distance between two components may be that is less than the wavelength of the amplified light. For example, the lateral dimension of the pillar body 120, the height of pillar body 120, the dimensions of metal disc 130, the distances between any gaps between metallic dot structures 140, the distances between metallic dot structure 140 and metallic disc 130 may be smaller than the wavelength of the amplified light. As illustrated in FIG. 1A, the pillars may be arranged on the substrate in the form of an array. In particular cases, the nearest pillars of the array may be spaced by a distance that is less than the wavelength of the light. The pillar array can be periodic and aperiodic.

The nanodevice may be disposed within a container, e.g., a well of a multi-well plate. The nanodevice also can be the bottom or the wall of a well of a multi-well plate. The nanodevices may be disposed inside a microfluidic channel (channel width of 1 to 1000 micrometers) or nanofluidic channel (channel width less 1 micrometer) or a part of inside wall of such channels.

As will be described in greater detail below (and as illustrated in FIG. 1C), a subject nanodevice 100 may be fabricated by coating a so-called "disc-coupled dots-an-pillar antenna array" 200 (i.e., a "D2PA", which is essentially composed of substrate 110 and a plurality of pillars that comprise pillar body 120, metallic disc 130, metallic back plane 150 and metallic dot structures 140 with a molecular adhesion layer 160. A detailed description an exemplary D2PA that can be employed in a subject nanodevice are provided in WO2012/024006, which is incorporated by reference herein for disclosure for all purposes.

The first part of the description that follows below describes certain features (i.e., the substrate, the pillar body, the metallic disc, the metallic back plane and the metallic dot structures) of the underlying D2PA structure. The second part of the description that follows below describes the molecular adhesion layer, the capture agents, and assays in which a subject nanonsensor can be employed.

Disc-Coupled Dots-on-Pillar Antenna Arrays (D2PA)

A disc-coupled dots-on-pillar antenna array has a 3D plasmon cavity antenna with a floating metallic disc or nanodisc that is coupled to nanoscale metallic dots on a pillar body. Specifically, in some embodiments the D2PA has a substrate, a pillar array on the substrate, a metallic disc or nanodisc on top of each of the pillars, nanoscale metallic dots on the pillar sidewall, with gaps between the disc and some of the dots, gaps between the neighboring dots, and a metallic back-plane which covers the most of the substrate areas that are not occupied by the pillars.

In one embodiment, the pillar array is fabricated from $SiO_2$ with a 200 nm pitch, 130 nm height, and 70 nm diameter on the substrate, formed from silicon. The metallic back-plane may be formed from a 40 nm thick layer of gold, deposited on the pillar array structures and substrate using e-beam evaporation along the normal direction. The deposition process forms the metallic discs in gold on top of each $SiO_2$ pillar while simultaneously forming the gold nanohole metallic back plane on the surface of the silicon substrate. Each disc has a thickness of 40 nm and diameter about 110 nm. During the evaporation process, with a deposition rate of about 0.4 Ns, the gold atoms diffuse onto the sidewalls of the $SiO_2$ pillars and congregate into random particles with granule sizes between 10 nm and 30 nm, forming the nanoscale metallic dots.

A substrate with the gold nanodiscs, random gold nanoparticle metallic dots, and bottom gold nanohole plate (backplane) is formed by the evaporation process. The gold nanoparticles scattered on the sidewall of the $SiO_2$ pillars, forming the nanoscale metallic dots, have narrow gaps of about 0.5 nm-20 nm between them, which can induce highly enhanced electrical fields. As used herein, the term "gap" is defined as the minimum spacing between the two structures, such as the minimum spacing between two discs or the spacing between a disc and an adjacent dot structure. It also should be pointed out that the even a part of a dot contacts with another dot, an enhancement effects achieved by the present structures still exist, since there are other gaps present between adjacent structures in other locations.

The D2PA structure can enhance light absorption through plasma resonance and nanoantennas. The structure can enhance a local electric field through the nanogaps between the discs and nanodots and the nanogaps (140) between the nanodots themselves, and assisted by the vertical cavity (for light) formed between the discs and the back plane, and the lateral cavity formed by the disc array.

More specifically, the structure can enhance the light absorption through the array of nanopillars, and can enhance the reflection of an optical signal from the surface through these structures. It may have an enhanced vertical cavity light absorption effect, formed by the discs through the dots and the back plane to enhance the light absorption. It also can have a lateral cavity light absorption effect through the back plane of the metal to enhance the light absorption. It will be recognized by those skilled in the art that any particular D2PA structure may have one, several, or all of these functions, depending upon the specific configuration of the structure, including the spacing in the pillar array, size of the pillars, size of the discs, size of the dots, and materials employed.

The enhancement of optical signals by the structure will be a product of enhancement from the nanogaps between features of the structure, from plasmon resonance, from antenna absorptions, from antenna radiations, from vertical cavities, as well as lateral cavities. The elements and functions of D2PA structure may be viewed from a different angle. The discs and the spacing gap between the disc and the adjacent metallic dots, as well as and between the dots themselves, can affect the local electric field enhancement provided by the structure. The dot position and number of dots on each pillar body can also enhance the local electric field. The diameter of each pillar and diameter of the capping disc can affect the plasmon resonant frequency. The silicon dioxide pillar height can affect the cavity length and number of nanogaps, and also can affect the coupling of the disc and the gold back planes. The number of pillars per unit cell can affect the active areas, and the pitch (spacing) in the array of pillars can affect coherent absorption and radiation of light. The gold back plane can affect the antenna and cavity, and the pillar shape can determine the light dependent absorption.

Within the structure, multiple variables may be "tuned" to enhance signals. For example, the diameter of the discs and shape of the pillars may be varied to alter the plasmon resonant frequency, the metallic dots will effect local signal enhancement, as well the disc-to-dot gap, dot position, and dot counts on each pillar body; the height of the pillars will affect the resonant cavity length and the number of nanogaps present, as well as the coupling effect between the disc and the metallic back plane. The total number of pillars per unit cell on the surface of the structure defines the active areas, and the pillar spacing (pitch) effects coherent absorption and radiation of optical energy. Finally, the metallic back plane material and thickness is related to antenna and cavity effects. Those of ordinary skill in this field will recognize that each of these variable may be altered as require from the exemplary embodiments shown herein to achieve a structure 100 having desired characteristics or "tuning" to achieve specific enhancements, without departing from the scope of the present invention.

A variety of configurations for the structure are envisioned. For example, the structure of the D2PA can have a layer of $SiO_2$ under the metal back plane and which contiguously forms the pillars. Alternatively, the D2PA having a metallic back plane without holes, such that the pillars are formed directly on the back plane material, which in turn is deposited over a layer of $SiO_2$ on the underlying substrate.

When constructing the D2PA structure of the present disclosure, the material for the underlying substrate can be an insulator, a semiconductor, or a dielectric insulator. The substrate need not be monolithic, but may be of a laminate construction, comprising an insulator or semiconductor material top layer (the layer next to the pillars) while the rest of the substrate is made of any solid material.

The pillar bodies on the top layer of the substrate may be formed from an insulating material, but may be semiconductors. Exemplary materials for the formation of the pillars are dielectrics: silicon-dioxide, silicon-nitride, hafnium oxide (HfO), Aluminum oxide (AlO) or semiconductors: silicon, GaAs, and GaN. Once formed, the pillars may have sidewalls which are columnar (straight), sloped, curved, or any combination thereof. The height of each pillar may be chosen from 5 nm to 7,000 nm, and a lateral dimension of each pillar may be chosen from 5 nm to 8,000 nm. The shape of the top surface of the pillar can be round, a point (of a pyramid), polygon, elliptical, elongated bar, polygon, other similar shapes or combinations thereof. The spacing between the pillars in the array can be periodic or aperiodic. For some applications, a periodic period is preferred and the period is chosen to maximize the light absorption and radiation, which is light wavelength dependent. The spacing (pitch) between adjacent pillars in the array may be from 4 nm to 4000 nm.

Each pillar is topped with a metallic disc which may be formed from either: (a) single element metal, such as gold, silver, copper, aluminum, nickels; (b) a combination of the multiplayer and/or multilayer of the single metals; (c) metallic alloys; (d) semiconductors, (e) any other materials that generate plasmons, or (f) any combination of (a), (b), (c), (d) and (e). The shape of each disc can be a rounded, pointed (as in the form of a pyramid or cone), polygonal, elliptical, elongated bar, polygon, other similar shapes or combinations thereof. The shape of each disc can be the same as, or different from, the shape of the top surface of the associated pillar on which it is disposed. Preferably, a lateral dimension of each disc is from 4 nm to 1500 nm, and a thickness of the disc is from 1 nm to 500 nm. The diameter of the metal discs can be either larger or smaller than the diameter of the supporting pillar. The diameter difference can various from 0 to 200 nm depending the working wavelength.

Disposed on the sidewalls of each pillar between the metallic disc and the metallic back plane, the metallic dots have shapes which are approximately spherical, discs-like, polygonal, elongated, other shapes or combinations thereof. The metallic dots on a pillar may all have approximately the same shape, or may be individually varied. The dimensions of the metallic dots are preferably between 3 nm to 600 nm, and may be different in three dimensions. The exact dimension of the dots may be selected for a specific light signal, as well regulated by fabrication convenience and the fabrication of the associated gaps there between.

In some embodiments, the gaps between the neighboring metallic dots and the gap between the disc and adjacent metallic dots is between 0.5 nm to 200 nm. For many applications, a small gap is preferred to enhance the optical signals. The gaps may be varied between each metallic dot on a pillar.

In the embodiment, the metallic back plane defines a metallic layer on the substrate with a hole for each pillar. The thickness of the metallic back plane is selected to be from 1 nm to 2000 nm, with a thickness in the range of 50 nm-200 nm preferred. The material of the metallic back plane can be selected from the same group as is used to form the metallic disc described above, but for a given D2PA structure, the metallic back plane can be formed from either the same or a different material as that used to form the discs.

The above descriptions of the D2PA structure are illustrative of the range of the materials, shapes, and dimensions which may be employed, but are not considered to be exclusive. Other materials, shapes, and dimensions may be used as required to achieve a desired enhancement effect. The exact materials, shapes, and dimensions for each D2PA structure will be determined by particular requirements imposed by the light absorption to be enhanced (wavelength, polarization), the light re-radiation to be enhanced, and/or the local electric field to be enhanced.

A D2PA array may be fabricated using the following method. The initial step is to provide the substrate with a layer of pillar material, such as $SiO_2$. The next step is to employ a lithographic imprinting process to imprint a mold having a pattern of pillars into a resist layer deposited over the layer of pillar material. After imprinting the pattern into the resist layer to create an etch mask, the residual material is removed via an etching process to leave a pattern of pillar-like structures of the resist layer. A layer of etch mask material, such as chromium (Cr) or other material is then deposited over the pattern of pillar-like structures, and the remaining resist material removed, resulting in a pattern of Cr deposited directly on the layer of pillar material. A final etching step which may be a dry etching such as retro-etching, or a wet etching process, removes the unprotected portions of pillar material, and leaves an array of pillars disposed on the surface of the substrate. Any remaining etch mask material (Cr) is optionally removed by either a dry or wet etching process, and an evaporation process is employed to deposit the metallic back plane material, disc material, and metallic dots onto the structure in a substantially collimated deposition.

Those of ordinary skill will recognize that the various lithography steps can use any variety of known lithography methods, including electron-beam lithography, ion beam lithography, photolithography, or nanoimprint lithography to form the pattern in the resist material. Similarly, it will be recognized that the etching mask material can be metal dielectric or insulators.

The etch mask material can be deposited on the resist layer before or after the lithography step is performed. A liftoff process will typically be used if the etch masking material is deposited after the lithography step. Alternatively, if the step of nanoimprint lithography is used to create a resist pattern first, an etch mask material may be subsequently deposited into the resulting trenches second, and then a liftoff process is performed. Other methods for making a D2PA array are possible.

Through manipulation of the various parameters of the D2PA structure, light of various wavelengths from about 100 nm to about 8000 nm may be manipulated.

The enhancement structure may be constructed with one or more features specific to the wavelength of light to be detected. These features include including the material selection, the nanoscale pillar height, the nanoscale pillar sidewall shape, the nanoscale metallic disc shape, the nanoscale metallic dot structure spacing, the metallic materials, and the metallic backplane configuration. The selection of the nanoscale metallic dot structure spacing further includes selecting a gap distance between adjacent nanoscale metallic dot structures and/or selecting a gap spacing between the nanoscale metallic disc and adjacent nanoscale metallic dot structures.

The substrate of the nanoscale structure may be an electrical insulator, a dielectric insulator or a semiconductor. Optionally the substrate may be a laminate structure, and wherein a layer at the surface of the substrate is either an electrical insulator or a semiconductor; and wherein a body of the substrate below the surface layer consists of any solid material.

The pillar bodies may be formed from either an insulator or a semiconductor, and has a top which has a shape selected from the group of shapes consisting of round, pointed, polygonal, pyramidal, elliptical, elongated bar shaped, or any combinations thereof. The sidewall surface of the pillar may be columnar, sloped, or curved. Preferably, the pillar has a height in the range from 5 nm to 7000 nm and a diameter in the range from 5 nm to 8000 nm. Optionally, the pillar may be part of an array of pillars extending from the surface of the substrate, with a spacing between adjacent pillars in the range from 2 nm to 4,000 nm. The array of pillars may define a periodic array with a spacing selected in relation to light of a selected wavelength in order to maximize absorption or radiation of the light using the nanoscale structure. Suitable materials for the formation of the pillars on the nanoscale structure include silicon-dioxide, silicon-nitride, hafnium oxide, aluminum oxide, silicon, gallium arsenide, and gallium nitride.

The metallic discs of the nanoscale structure are formed on top of the pillars from a metal such as gold, silver, copper, aluminum, alloys thereof, or combinations thereof. The surface of the metallic discs need not be uniform, and may have any configuration such as round, pointed, polygonal, elliptical, bar or combinations thereof. Preferably, a lateral dimension of the metallic disc is in the range from 5 nm to 1500 nm and a vertical thickness of the metallic disc is in the range from 1 nm to 500 nm.

The metallic dot structures disposed on the pillar sidewalls of the nanoscale structure each have a shape selected from a group of shapes consisting of approximately spherical, circular, polygonal, elongated or combinations thereof, and have dimensions in the range 3 nm to 600 nm. A gap between the metallic dot structures and the metallic disc on a common pillar is in a range from 0.5 nm to 600 nm, as is the gap between adjacent metallic dot structures.

The metallic back plane of the nanoscale structure may be configured either with holes through which the pillar bodies extend from surface of the substrate, or may be substantially continuous, with the pillar bodies disposed there on. Preferably, the metallic back plane has a thickness ranging from 1 nm to 2000 nm, e.g., from 50 nm to 200 nm, and is composed of a metal selected from the group of metals consisting of gold, silver, copper, aluminum, alloys thereof, or combinations thereof. The metallic back plane may be formed from either the same material as, or a different material from, the metallic discs.

The nanoscale structure of the present disclosure may be made by a variety of methods. An exemplary method for manufacture of the nanoscale structure for enhancing local electric fields, absorbing light or radiating light comprises the steps of: providing a substrate comprising an outer surface of insulating or semiconductive material; forming on the outer surface an array of pillars having a height in the range 5 nm to 7000 nm and a lateral dimension in the range 5 nm to 8000 nm; applying conductive material to the tops of the pillars and to the underlying substrate; and simultaneously (or subsequently) depositing conductive dot structures on the pillar sidewalls. The array of pillars is formed by a process comprising electron beam lithography, ion-beam lithography, photolithography or nanoimprint lithography.

In one embodiment that is configured for enhance light at a wavelength of ~800 nm, the D2PA nanostructure may be composed of a periodic non-metallic (e.g. dielectric or semiconductor) pillar array (200 nm pitch and ~100 nm diameter), a metallic disk (~135 nm diameter) on top of each pillar, a metallic backplane on the foot of the pillars, metallic nanodots randomly located on the pillar walls, and nanogaps between these metal components. The disk array and the backplane (both are 55 nm thick) form a 3D cavity antenna that can efficiently traps the excitation light vertically and laterally. Each pillar has about 10 to 50 nanodots depending upon the pillar geometry; and the pillar density is $2.5 \times 10^9$ pillars/cm$^2$.

The device may be configured to detect light having a wavelength in the range of 400 to 1,000 nm range. In certain embodiments, the average diameter for the nanodots is in the range of 1 nm to 25 nm, and gaps between the nanodots, and the gaps between the nanodots and the nanodisks may be in the range of 1 nm to 10 nm. The metal is selected from the group consisting of gold, silver, copper, aluminum, alloys thereof, and combinations thereof. The top of the pillar has a shape selected from the group of shapes consisting of round, polygonal, pyramidal, elliptical, elongated bar shaped, or any combination thereof. The lateral dimension of the metallic disc is in the range from 5 nm to 150 nm. The metallic disc and the metallic back plane are spaced by a distance in the range of 0.1 nm to 60 nm. At least one metallic dot structure has dimensions in the range of 1 nm to 25 nm. The distance between the metallic dot structure the metallic disc, and the distance between the metallic dot structure and the metallic backplane are spaced by a distance in the range of 0.5 nm to 50 nm.

In particular embodiments, the spacing between the two nearest pillars of the plurality of pillars is in the range from 2 nm to 200 nm. The pillar has a sidewall surface that is columnar, sloped, or curved. The thickness of the metallic disc and metallic back plane is between 5 nm to 60 nm. The pillar has a lateral dimension or a height less than the wavelength of the light. The metallic disc has substantially the same lateral geometry as the pillar. The pillar comprises a dielectric or semiconductor material selected from the group consisting of polymers, silicon-dioxide, silicon-nitride, hafnium oxide, aluminum oxide, silicon, gallium arsenide, and gallium nitride. The lateral dimension of the metallic disc is less than the wavelength of the light.

Figure 21:
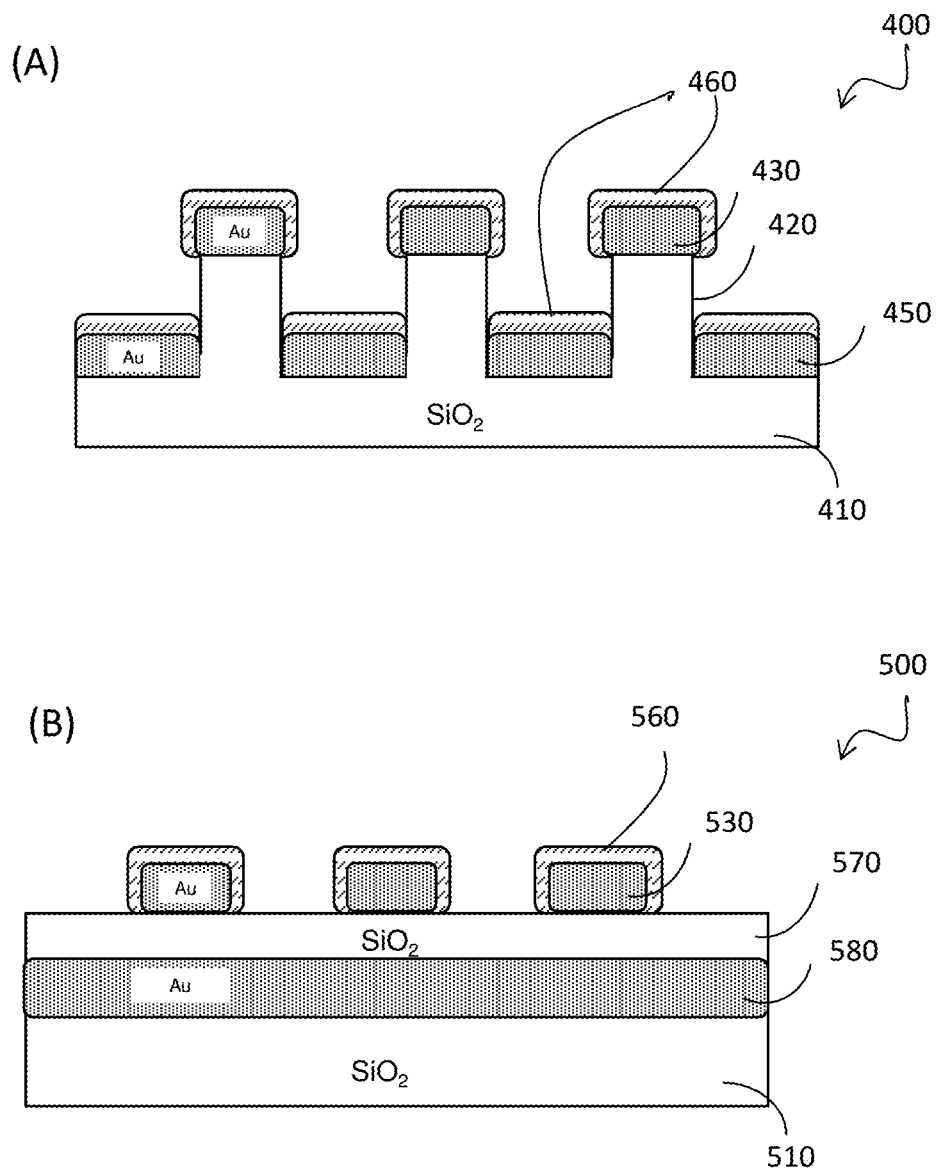
FIG. 21 schematically illustrates an alternative embodiment.

FIG. 21 shows two alternative embodiments, in which embodiment (A) 400, there are no metallic dot structure on pillar sidewall, but only the pillars 415 and the metallic disk 430 on top of the pillars and the metallic back plane 450 on the foot of the pillars, and the molecular adhesion layers 460 coated to the disks and the back plane. It has a substrate 410, In embodiment (B) 500, there are no pillar and metallic dot structure, but only a metallic back plane 570 which now is a thin metal film 580 on a dielectric or semiconductor substrate 510 with a thin film of an dielectric (e.g. SiO2) or semiconductor 580 on top of the metal back plane, and finally metallic disks and the molecular adhesion layers 560 coated to the disks only. It has a substrate 510, The shape and size (lateral dimension and its thickness) of the metallic disk are in similar to that in D2PA. For the embodiment (A), the pillars and the backplane are similar to the in D2PA. For the embodiment (B), the materials for the thin dielectric and semincoductor layer are similar to the materials for the pillars, but the film thickness is from 0.5 nm to 150 nm; and there is no limitation on the thickness of the back plane (except no thinner than 2 nm). In both embodiments, the materials for the metals are similar to that in D2PA, except in the embodiment (B) two dissimilar materials can be used for the disk and the back plane.

Molecular Adhesion Layer and Attachment of Capture Agents

As shown in FIG. 1, nanodevice 100 comprises a molecular adhesion layer 160 that covers at least a part of the metal surfaces of the underlying D2PA. The molecular adhesion layer has two purposes. First, the molecular adhesion layer acts a spacer. For optimal fluorescence, the light-emitting labels (e.g., fluorophores) cannot be too close to the metal surface because non-radiation processes would quench fluorescence. Nor can the light-emitting labels be too far from the metal surface because it would reduce amplification. Ideally, the light-emitting labels should be at an optimum distance from the metal surface. Second, the molecular adhesion layer provides a good adhesion to attach capture agent onto the nanodevice. The good adhesion is achieved by having reactive groups in the molecules of the molecular adhesion layer, which have a high affinity to the capture agent on one side and to the nanodevices on the other side.

The molecular adhesion layer (MAL) 160 can have many different configurations, including (a) a self-assembled monolayer (SAM) of cross-link molecules, (b) a multi-molecular layers thin film, (c) a combination of (a) and (b), and (d) a capture agent itself.

Figure 3:
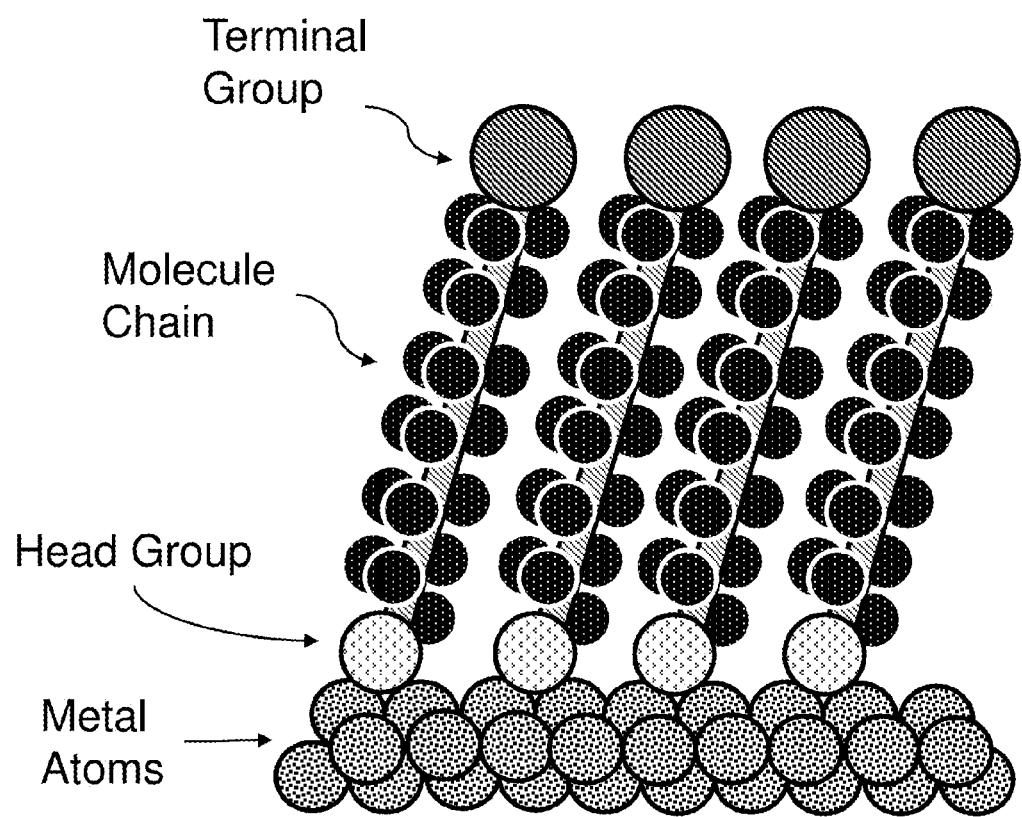
FIG. 3 schematically illustrates an exemplary self-assembled monolayer.

In the embodiment of MAL (a), where the molecular adhesion layer 160 is a self-assembled monolayer (SAM) of cross-link molecules or ligands, each molecule for the SAM comprises of three parts: (i) head group, which has a specific chemical affinity to the nanodevice's surface, (ii) terminal group, which has a specific affinity to the capture agent, and (iii) molecule chain, which is a long series of molecules that link the head group and terminal group, and its length (which determines the average spacing between the metal to the capture agent) can affect the light amplification of the nanodevice. Such a SAM is illustrated in FIG. 3.

In many embodiments, the head group attached to the metal surface belongs to the thiol group, e.t., —SH. Other alternatives for head groups that attach to metal surface are, carboxylic acid (—COOH), amine (C=N), selenol (—SeH), or phosphane (—P). Other head groups, e.g. silane (—SiO), can be used if a monolayer is to be coated on dielectric materials or semiconductors, e.g., silicon.

In many embodiments, the terminal groups can comprise a variety of capture agent-reactive groups, including, but not limited to, N-hydroxysuccinimidyl ester, sulfo-N-hydroxy-succinimidyl ester, a halo-substituted phenol ester, pentafluorophenol ester, a nitro-substituted phenol ester, an anhydride, isocyanate, isothiocyanate, an imidoester, maleimide, iodoacetyl, hydrazide, an aldehyde, or an epoxide. Other suitable groups are known in the art and may be described in, e.g., Hermanson, "Bioconjugate Techniques" Academic Press, 2nd Ed., 2008. The terminal groups can be chemically attached to the molecule chain after they are assembled to the nanodevice surface, or synthesized together with the molecule chain before they are assembled on the surface.

Other terminal groups are Carboxyl —COOH groups (activated with EDC/NHS to form covalent binding with —NH2 on the ligand); Amine, —NH2, group (forming covalent binding with —COOH on the ligand via amide bond activated by EDC/NHS); Epoxy, Reacted with the —NH2 (the ligand without the need of a cross-linker); Aldehyde, (Reacted with the —NH2 on the ligand without the need of a cross-linker); Thiol, —SH, (link to —NH2 on the ligand through SMCC-like bioconjugation approach); and Glutathione, (GHS) (Ideal for capture of the GST-tagged proteins.

The molecular chain can be carbon chains, their lengths can be adjusted to change the distance between the light emitting label to the metal for optimizing the optical signal. In one embodiment, as will be described in greater detail in example section, the SAM layer is dithiobis(succinimidyl undecanoate), whose head group is —SH that binds to gold surface through sulfer-gold bond, and terminal group is NHS-ester that bind to the primary amine sites of the capture agent, and the molecule alkane chain with length of 1.7 nm.

In many embodiments, the molecule chains that link head groups and terminal groups are alkane chain, which is composed of only hydrogen and carbon atoms, with all bonds are single bonds, and the carbon atoms are not joined in cyclic structures but instead form a simple linear chain. Other alternatives for molecule chain can be ligands that are from polymers such as poly(ethylene glycol) (PEG), Poly (lactic acid) (PLA), etc. The molecule chains are chemically non-reactive to neither the metal surface that the head groups attach to, nor the capture agent that the terminal groups attach to. The chain length, which determines the distance of analyte to the nanodevice's surface, can be optimized in order to achieve the maximum signal amplification. As will be described in greater detail below, the molecule chains may have a thickness of, e.g., 0.5 nm to 50 nm.

The molecular adhesion layer used in the subject nanosensor may be composed of a self-assembled monolayer (SAM) that is strongly attached to the metal at one side (via, e.g., a sulfur atom) and that terminates a capture-agent-reactive group, e.g., an amine-reactive group, a thiol-reactive group, a hydroxyl-reactive group, an imidazolyl-reactive group and a guanidinyl-reactive group, at the other (exterior) side. The monolayer may have a hydrophobic or hydrophilic surface. The most commonly used capture-agent reactive groups are NHS (which is amine-reactive) and maleimide (which is sulfhydrl-reactive), although many others may be used.

In some embodiments, the molecular adhesion layer may be a self-assembled monolayer of an alkanethiol (see, e.g., Kato Journal of Physical Chemistry 2002 106: 9655-9658), poly(ethylene)glycol thiol (see, e.g., Shenoy et al Int. J. Nanomedicine. 2006 1: 51-57), an aromatic thiol or some other chain that terminates in the thiol.

Thiol groups may be used because (a) the thiol sulfur interacts with gold and other metals to form a bond that is both strong and stable bond (see, e.g., Nuzzo et al J. Am. Chem. Soc. 1987 109:2358-2368) and (b) van der Waals forces cause the alkane and other chains chains to stack, which causes a SAM to organize spontaneously (see, e.g., Love et al. Chem. Rev. 2006 105:1103-1169). Further, the terminal group is available for either direct attachment to the capture molecule or for further chemical modifications.

Alkanethiol may be used in some embodiments. It has been estimated that there are $4 \times 10^{14}$ alkanethiol molecules/$cm^2$ in a packed monolayer of alkanethiol (Nuzzo et al, J. Am. Chem. Soc. 1987 109:733-740), which approximately corresponds to an alkanethiol bond to every gold atom on the underlying surface. Self-assembled monolayers composed of alkanethiol can be generated by soaking the gold substrate in an alkanethiol solution (see, e.g., Lee et al Anal. Chem. 2006 78: 6504-6510). Gold is capable of reacting with both reduced alkanethiols (—SH groups) and alkyldisulfides (—S—S—) (see, e.g., Love et al Chem. Rev. 2005 105: 1103-1169).

Once a self-assembled monolayer of poly(ethylene)glycol thiol or alkanethiol has been produced, a large number of strategies can be employed to link a capture to the self-assembled monolayer. In one embodiment, a capture agent such as streptavidin (SA) can be attached to the SAM to immobilize biotinylated capture agents.

In one embodiment, streptavidin (SA) itself can be use as a functional group (e.g. terminal group) the SAM to cross-link capture agent molecules that have high binding affinity to SA, such as biotinylated molecules, including peptides, oligonucleotides, proteins and sugars.

The functional group of avidin, streptavidin have a high affinity to the biotin group to form avidin-biotin. Such high affinity makes avidin/streptavidin serve well as a functional group and the biotin group as complementary functional group binding. Such functional group can be in binding the molecular adhesion layer to the nanodevice, in binding between molecular adhesion layer and the capature agent, and in binding a light emitting lable to the secondary capture agent. In one embodiment, a molecular adhesion layer containing thiol-reactive groups may be made by linking a gold surface to an amine-terminated SAM, and further modifying the amine groups using sulfosuccinimidyl-4-(N-maleimidomethyl)cyclohexane-1-carboxylate (Sulfo-SMCC) to yield a maleimide-activated surface. Maleimide-activated surfaces are reactive thiol groups and can be used to link to capture agents that contain thiol—(e.g., cysteine) groups.

In another embodiment, a molecular adhesion layer containing an amine-reactive group (N-hydroxl succinimide (NHS)) can be produced by, e.g., by soaking the gold substrate in a 1-10 mM solution of succinimidyl alkanedisulfides such as dithiobis-sulfosuccinimidylpropionate (DSP) or dithiobis(succinimidyl undecanoate) (see, e.g., Peelen et al J. Proteome Res. 2006 5:1580-1585 and Storri et al Biosens. Bioelectron. 1998 13: 347-357).

In another embodiment, a molecular adhesion layer containing an amine-reactive group (NHS) may be produced using carboxyl-terminated SAM such as 12-carboxy-1-un-decanethiol. In this case, the surface of the SAM may be linked to the NHS in the presence of 1-ethyl-3(3dimethyl-aminopropyl)carbodiimide HCl (EDC) to yield an intermediate which forms stable amide bonds with primary amines (see, e.g., Johnsson et al Anal. Biochem. 1001 198: 268-277).

In another embodiment, a molecular adhesion layer may contain Protein A which binds with high affinity to Fc region of IgGs, other immunoglobulin form, e.g., IgE.

In another embodiment, an imidazole group (which is also reactive with amines) may be added by reacting a carboxyl-terminated SAM with 1,1'-carbonyldiimidazole (CDI).

In further embodiments, aldehyde-terminated alkanethiol monolayers can be used to immobilize both proteins and amine-terminated DNA oligonucleotides, and his-tagged fusion proteins can be immobilized on nitrilotriacetic (NTA)-modified gold surfaces.

Thiol-reactive groups can link to synthetic DNA and RNA oligonucleotides, including aptamers, which can be readily synthesized commercially with a thiol terminus. Thiol-reactive groups can also link to proteins that contain a cysteine groups, e.g., antibodies. Thiolated molecules can be attached to maleimide-modified surfaces (see, e.g., Smith et al Langmuir 2002 19: 1486-1492). For in certain cases, one may use an amino acid spacer (e.g., Ser-Gly-Ser-Gly) inserted after a terminal Cys, which improves the amount of binding relative peptides that lacking spacers. For oligonucleotides, an alkane spacer can be used. Carbohydrates synthesized to contain with terminal thiols can be been tethered to gold in the same way.

Amine-reactive groups can form bonds with primary amines, such as the free amine on lysine residues. In addition to proteins, amine-reactive surfaces can be used to immobilize other biomolecules, including peptides containing lysine residues and oligonucleotides synthesized with an amine terminus.

In the embodiment of MAL (b), in which the molecular adhesion layer 160 is a multi-molecular layer thin film, the molecules may be coated on the D2PA nanodevice through physical adsorption or strong binding. In one example, protein A can be coated over the entire or partial areas of the surface of D2PA nanodevice surface, in which case the protein A can be deposited through physical adsorption process and has a thickness of 4 nm to 5 nm. In another example, the layer may be a thin film of a polymer such as polyethylene glycol (PEG), which has a functional head group on one end, e.g., thiol (—SH). The functioned PEG molecule layer forms a strong bond to D2PA nanodevice's surface. The thickness of PEG molecule layer can be tuned by changing the PEG polymer chain length. Another example is an amorphous SiO2 thin film, which is attached to the surface of the D2PA nanodevice using physical or chemical deposition methods, e.g., evaporation, sputtering, sol-gel method. The thickness of the SiO2 thin film can be precisely controlled during the deposition.

In the embodiment of MAL (c), where the molecular adhesion layer 160 is a combination of a multi-molecular layer thin film and a SAM, the SAM layer may be deposited first, followed by a multi-molecular layer.

In one example, the molecular adhesion layer may contain a monolayer of streptavidin first, followed by other layers of molecules that have high binding affinity to streptavidin, such as biotin, biotinylated molecules, including peptides, oligonucleotides, proteins, and surgars.

In one example, the molecular adhesion layer, may contain a SAM layer dithiobis(succinimidyl undecanoate) (DSU) and a Protein A layer. The DSU SAM layer binds to nanodevice's metal surface through sulfer-gold bond, and has a terminal group of NHS-ester that binds to the primary amine sites on Protein A. In a particular case, capture antibodies bond to such bilayer of protein A on top of DSU through their Fc region. The protein A can ensure the orientation of antibodies for better capture efficiency.

In the embodiment of MAL (d), where the molecular adhesion layer 160 is a capture agent itself, the capture agent has a headgroup that have a high affinity to the metal or pillar sidewall of the subject nanodevice (i.e. D2PA). One of the common headgroup is thiol-reactive group. Thiol-reactive groups can link to synthetic DNA and RNA oligonucleotides, including aptamers, which can be readily synthesized commercially with a thiol terminus. Thiol-reactive groups can also link to proteins that contain a cysteine groups, e.g., antibodies. Another example where the MAL itself is used as the capture agent is a layer of antibody fragments, e.g., half-IgG, Fab, F(ab')2, Fc. The antibody fragments bond to metal surface directly through the thiol-endopeptidase located in the hinge region. This embodiment is illustrated in FIG. 6. In this embodiment, the nucleic acid comprises a headgroup that binds directly the nanodevice. The remainder of the steps are performed as described in FIG. 5.

The thickness of molecular adhesion layer should be in the range of 0.5 nm to 50 nm, e.g., 1 nm to 20 nm. The thickness of the molecular adhesion layer can be optimized to the particular application by, e.g., increasing or decreasing the length of the linker (the alkane or poly(ethylene glycol) chain) of the SAM used. Assuming each bond in the linker is 0.1 nM to 0.15 nM, then an optimal SAM may contain a polymeric linker of 5 to 50 carbon atoms, e.g., 10 to 20 carbon atoms in certain cases.

A nanosensor may be made by attaching capture agents to the molecular adhesion layer via a reaction between the capture agent and a capture-agent reactive group on the surface of the molecular adhesion layer.

Capture agents can be attached to the molecular adhesion layer via any convenient method such as those discussed above. In many cases, a capture agent may be attached to the molecular adhesion layer via a high-affinity strong interactions such as those between biotin and streptavidin. Because streptavidin is a protein, streptavidin can be linked to the surface of the molecular adhesion layer using any of the amine-reactive methods described above. Biotinylated capture agents can be immobilized by spotting them onto the streptavidin. In other embodiments, a capture agent can be attached to the molecular adhesion layer via a reaction that forms a stong bond, e.g., a reaction between an amine group in a lysine residue of a protein or an aminated oligonucleotide with an NHS ester to produce an amide bond between the capture agent and the molecular adhesion layer. In other embodiment, a capture agent can be strongly attached to the molecular adhesion layer via a reaction between a sulfhydryl group in a cysteine residue of a protein or a sulfhydrl-oligonucleotide with a sulfhydryl-reactive maleimide on the surface of the molecular adhesion layer. Protocols for linking capture agents to various reactive groups are well known in the art.

In one embodiment, capture agent can be nucleic acid to capture proteins, or capture agent can be proteins that capture nucleic acid, e.g., DNA, RNA. Nucleic acid can bind to proteins through sequence-specific (tight) or non-sequence specific (loose) bond.

In certain instances, a subject nanodevice may be fabricated using the method: (a) patterning at least one pillar on a top surface of a substrate; (b) depositing a metallic material layer of the top surface; (c) allowing the metallic material deposited on the pillar tops to form a disc, the metallic material deposited on the pillar feet to form a metallic back plane, and the metallic material deposited on the sidewall to form at least one metallic dot structure; and, as described above, (d) depositing a molecular adhesion layer on top of the deposited metallic material, wherein the molecular adhesion layer covers at least a part of the metallic dot structure, the metal disc, and/or the metallic back plane, and wherein the exterior surface of the molecular adhesion layer comprises a capture agent-reactive group.

Furthermore, the patterning in (a) include a direct imprinting (embossing) of a material, which can be dielectric or semiconductor in electric property, and can be polymers or polymers formed by curing of monomers or oligomers, or amorphous inorganic materials. The material can be a thin film with a thickness from 10 nanometer to 10 millimeter, or multilayer materials with a substrate. The imprinting (i.e. embossing) means to have mold with a structure on its surface, and press the mold into the material to be imprinted to for an inverse of the structure in the material. The substrates or the top imprinted layers can be a plastic (i.e. polymers), e.g. polystyring (PS), Poly(methyl methacrylate) (PMMA), Polyethylene terephthalate (PET), other acrylics, and alike. The imprinting may be done by roll to roll technology using a roller imprinter. Such process has a great economic advantage and hence lowering the cost.

Nanosensors

A nanosensor made by the method set forth above is provided. In certain embodiments, the nanosensor comprises (a) a substrate; and (b) one or a plurality of pillars extending from a surface of the substrate, wherein at least one of the pillars comprises: i. a metallic disc on top of the pillar; ii. a metallic back plane at the foot of the pillar, the metallic back plane covering a substantial portion of the substrate surface near the foot of the pillar; iii. a metallic dot structure disposed on sidewall of the pillar; iv. a molecular adhesion layer that covers at least a part of the metallic dot structure, the metal disc, and/or the metallic back plane; and v. a capture agent that specifically binds to an analyte, wherein the capture agent is linked to the molecular adhesion layer. The nanosensor is characterized in that it amplifies a light signal from an analyte, when the analyte is bound to the capture agent.

The light amplication comes from one or several following factors: the nanosensor can (a) absorb light excitation effectively (e.g. the light at a wavelength that excites fluorescent moieties), (b) focus the absorbed light into certain locations, (c) place the analytes into the regions where most of light are focused, and (d) radiate efficiently the light generated by analytes from the locations where the analytes immobilized.

Figure 4:
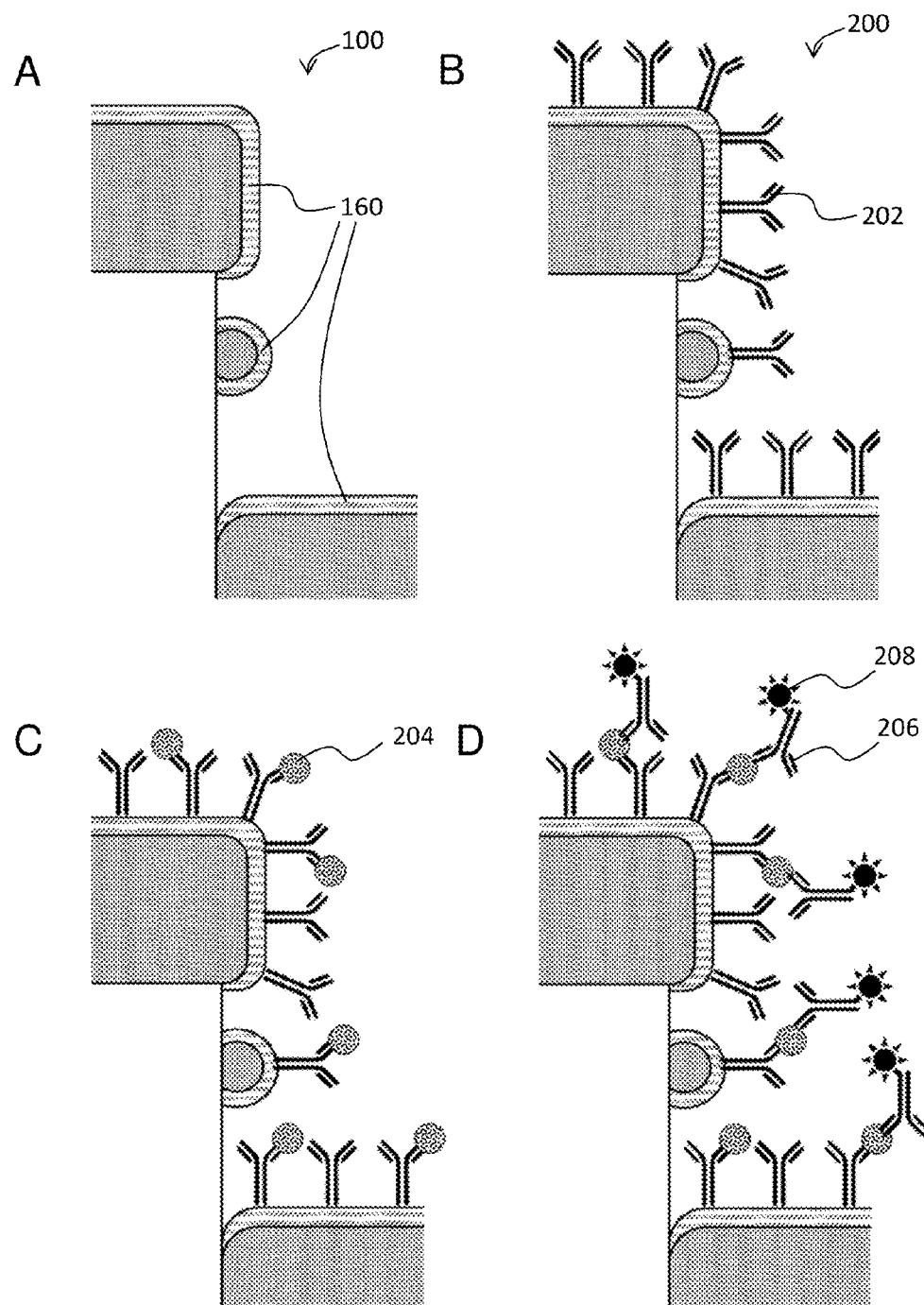
FIG. 4 schematically illustrates an exemplary antibody detection assay.

Depending on how the analyte is labeled, light signal that is amplified may be luminescence (e.g., chemiluminescent or electroluminescent, or fluorescence). FIG. 3 illustrates a biosensor in which the capture agent is a protein, e.g., an antibody; FIG. 4 illustrates a biosensor in which the capture agent is a nucleic acid, e.g., an oligonucleotide. In some embodiments, the thickness of the molecular adhesion layer is selected to optimize the amplification of the light signal.

In some embodiments, different capture agents are attached to the nanosensor surface with each capture agent coated on a different location of the surface, e.g., in the form of an array, hence providing multiplexing in detections of different analysts, since each location is specific for capturing a specific kind of analyte.

In some embodiments, the nanosensor may be implemented in a multi-well format, e.g., a 24-well, a 96-well or 384 well format, where each well of a multi-well plate comprises a nanosensor (e.g. the nanosensor is in each of the wells or is the bottom or a part sidewall of each well). The capture agent in each well can be the same or different. In some embodiments, multiple different capture agents, each coated on different location can be placed in a well, which provide multiplexing of detections for different analyst. In these embodiments, several analytes in a sample may be analyzed in parallel. In some embodiments, the nanosensor can be a part of micro or nanofluidic channel.

In particular embodiments, a subject nanosensor may further comprise labeled analyte that is specifically bound to the capture agent. As noted above, the labeled analyte may be directly or indirectly labeled with a light-emitting label. In embodiments in which an analyte is indirectly labeled with a light-emitting label, the analyte may be bound to a second capture agent, also termed: detection agent (e.g., a secondary antibody or another nucleic acid) that is itself optically labeled. The second capture agent may be referred to as a "detection agent" in some cases.

In other embodiments, a subject nanosensor may be disposed inside a microfluidic channel (channel width of 1 to 1000 micrometers) or nanofluidic channel (channel width less 1 micrometer) or a part of inside wall of such channels. The nanosensors may be disposes at multiple locations inside each channel and be used in multiple channels. The nanosensors in different locations or different fluidic channels may later coated with different capture agents for multiplexing of detections.

Systems

Also provided is a system comprising a subject nanosensor, a holder for the nanosensor, an excitation source that induces a light signal from a label (i.e. light emitting label); and a reader (e.g., a photodetector, a CCD camera, a CMOS camera, a spectrometer or an imaging device capable of producing a two dimensional spectral map of a surface of the nanosensor) adapted to read the light signal. As would be apparent, the system may also has electronics, computer system, software, and other hardware that amplify, filter, regulate, control and store the electrical signals from the reader, and control the reader and sample holder positions. The sample holder position can be move in one or all three orthogonal directions to allow the reader to scan the light signal from different locations of the sample.

Figure 2:
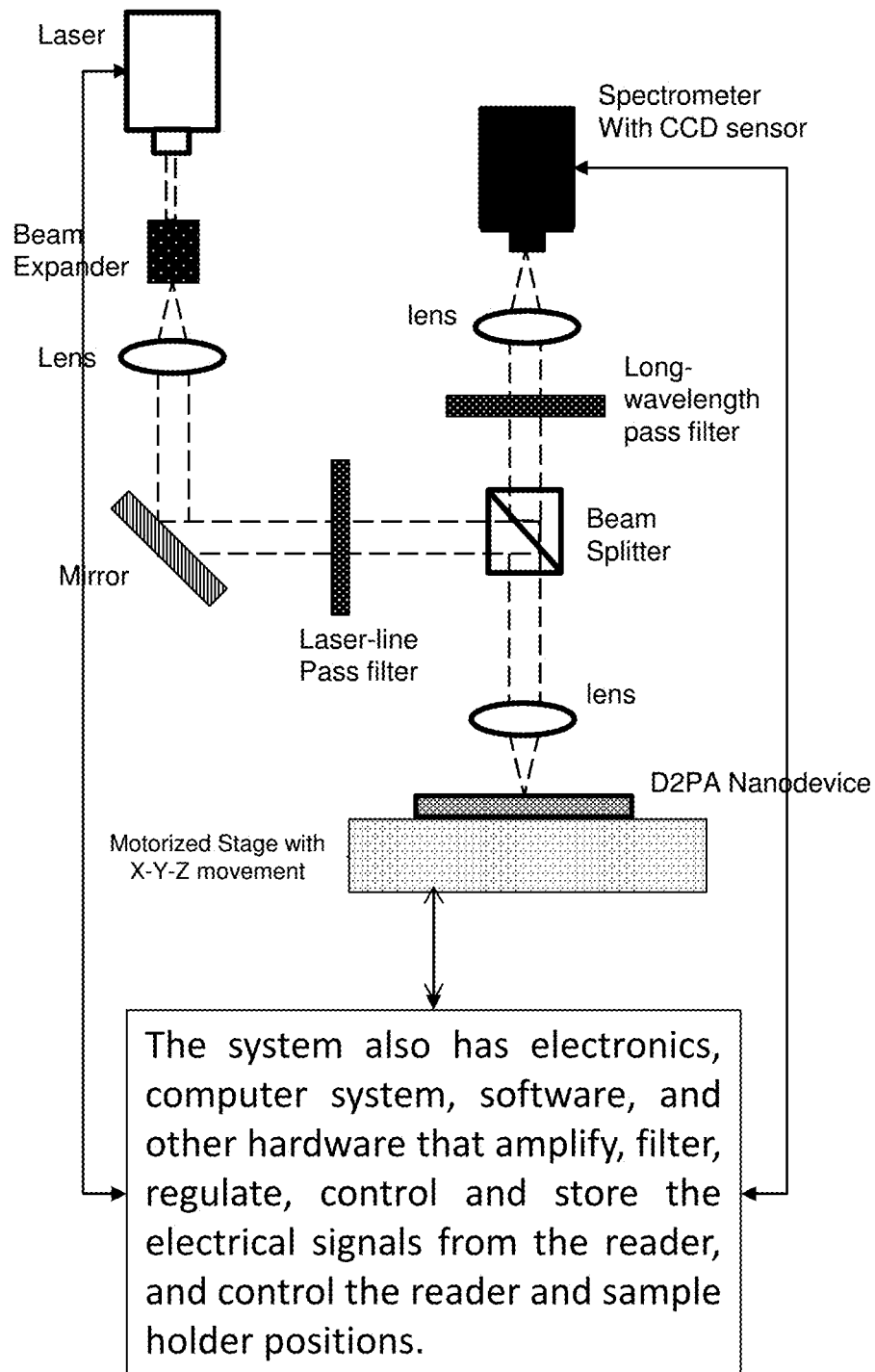
FIG. 2 schematically illustrates an exemplary system.

The excitation source may be (a) a light source, e.g., a laser of a wavelength suitable for exciting a particular fluorophore, and a lamp or a light emitting diode with a light filter for wavelength selection; or (b) a power source for providing an electrical current to excite light out of the nanosensor (which may be employed when an electrochemiluminescent label is used). An exemplary system is illustrated in FIG. 2. With reference to FIG. 2, the excitation system may comprise a laser, laser optics (including a beam expander, lens, mirror and a laser line-pass filter), a reader (e.g., a spectrometer with a CCD sensor), further optics (e.g., a long wavelength pass filter, a beam splitter, and a lens), and a holder for the nanosensor. In certain cases, the holder may be on a motorized stage that has an X-Y and Z movement.

In particular cases, laser-line pass filter filters out light whose wavelength is different from the laser, and the long wavelength pass filter will only allow the light emanate from the optically detectable label to pass through. Since different fluorescence labels absorb light in different spectral range, the fluorescence label should be chosen to match its peak absorption wavelength to the laser excitation wavelength in order to achieve optimum quantum efficiency. In many embodiments, the light signal emanating from the fluorescence label on the nanosensors are at a wavelength of at least 20 nm higher than the laser wavelength. Thus the nanosensor's plasmonic resonance should be tuned to cover the fluorescence label's absoprtion peak, emission peak and laser excitation wavelength. In some embodiments, the excitation and fluorescence wavelength range can be from 100 nm to 20,000 nm. The preferred range is from 300 nm to 1200 nm. The 600-850 nm range is preferable due to low background noise.

As would be apparent from the above, certain nanosensors may be implemented in a multi-well format. In these embodiments, the stage can move moved so that reader can read a light signal from each of the wells of the multi-well plate, independently.

Assay Methods

The subject nanosensor may be used to detect analytes in a sample. This method may comprise: (a) contacting a sample comprising an analyte with a nanosensor under conditions suitable for specific binding of an analyte in the sample with the capture agent; and (b) reading an optically detectable signal from the nanosensor, wherein the optically detectable signal indicates that the analyte is bound to the capture agent. In the above step (a), before the bonding to the capture agent, the the analyte may be labeled with a light-emitting label or not labeled (also referred as labeled directly or indirectly). In embodiments in which an analyte is no labeled with a light-emitting label before the bonding, the analyte, after the bonding to the capture agent, may be bound to a second capture agent (i.e. detection agent) (e.g., a secondary antibody or another nucleic acid) that is itself optically labeled, labeled secondary capture agent or labeled detection agent, (such process is also referred as indirectly labeling of an analyte). In a sensing using indirectly labeling, the labeled secondary capture agents unbounded to analytes are removed before the above reading step (b). In a sensing using directly labeling, the optical labels unbounded to analytes are removed before the above reading step (b).

In reading the light emitting labels on the assay, an excitation (photo, electro, chemical or combination of them) are applied to light emitting label, and the properties of light including intensity, wavelength, and location are detected.

In certain embodiments, the method comprises attaching a capture agent to the molecular adhesion layer of a subject nanodevice to produce a nanosensor, wherein the attaching is done via a chemical reaction of the capture agent with the capture agent-reactive group in the molecules on the molecular adhesion layer, as described above. Next, the method comprises contacting a sample containing a target-analyte with the nanosensor and the contacting is done under conditions suitable for specific binding and the target-analyte specifically binds to the capture agent. After this step, the method comprises removing any target-analytes that are not bound to the capture agent (e.g., by washing the surface of the nanosensor in binding buffer); Then detection agent conjugated with optical detectable label is added to detect the target-analyte. After removing the detection agent that are not bound to the target-analyte, The the nanodevice can then be used, with a reading system, to read a light signal (e.g., light at a wavelength that is in the range of 300 nm to 1200 nm) from detection agent that remain bound to the nanosensor. As would be apparent, the method further comprises labeling the target analytes with a light-emitting label. This can be done either prior to or after the contacting step, i.e., after the analytes are bound to the capture agent. In certain embodiments, analytes are labeled before they are contacted with the nanosensor. In other embodiment, the analytes are labeled after they are bound to the capture agents of the nanosensor. Further, as mentioned above, the analyte may be labeled directly (in which case the analyte may be strongly linked to a light-emitting label at the beginning of the method), or labeled indirectly (i.e., by binding the target analytes to a second capture agent, e.g., a secondary antibody that is labeled or a labeled nucleic acid, that specifically binds to the target analyte and that is linked to a light-emitting label). In some embodiments, the method may comprise blocking the nanosensor prior to the contacting step (b), thereby preventing non-specific binding of the capture agents to non-target analytes.

The suitable conditions for the specific binding and the target-analyte specifically binds to the capture agent, include proper temperature, time, solution pH level, ambient light level, humidity, chemical reagent concentration, antigen-antibody ratio, etc.

In certain embodiments, a nucleic acid capture agent can be used to capture a protein analyte (e.g., a DNA or RNA binding protein). In alternative embodiments, the protein capture agent (e.g., a DNA or RNA binding protein) can be used to capture a nucleic acid analyte.

The sample may be a liquid sample and, in certain embodiments, the sample may be a clinical sample derived from cells, tissues, or bodily fluids. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

Figure 5:
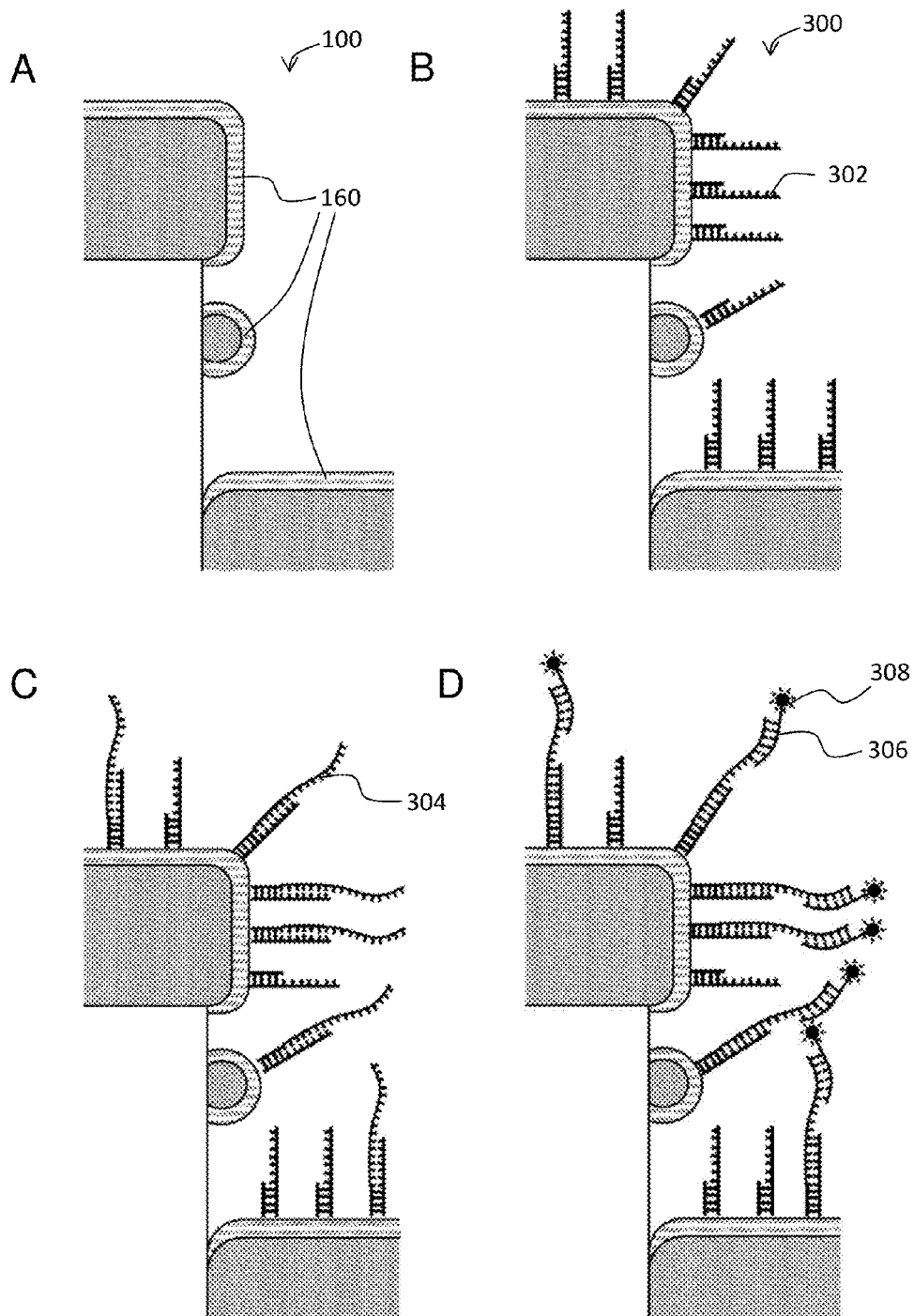
FIG. 5 schematically illustrates an exemplary nucleic acid detection assay.
Figure 6:
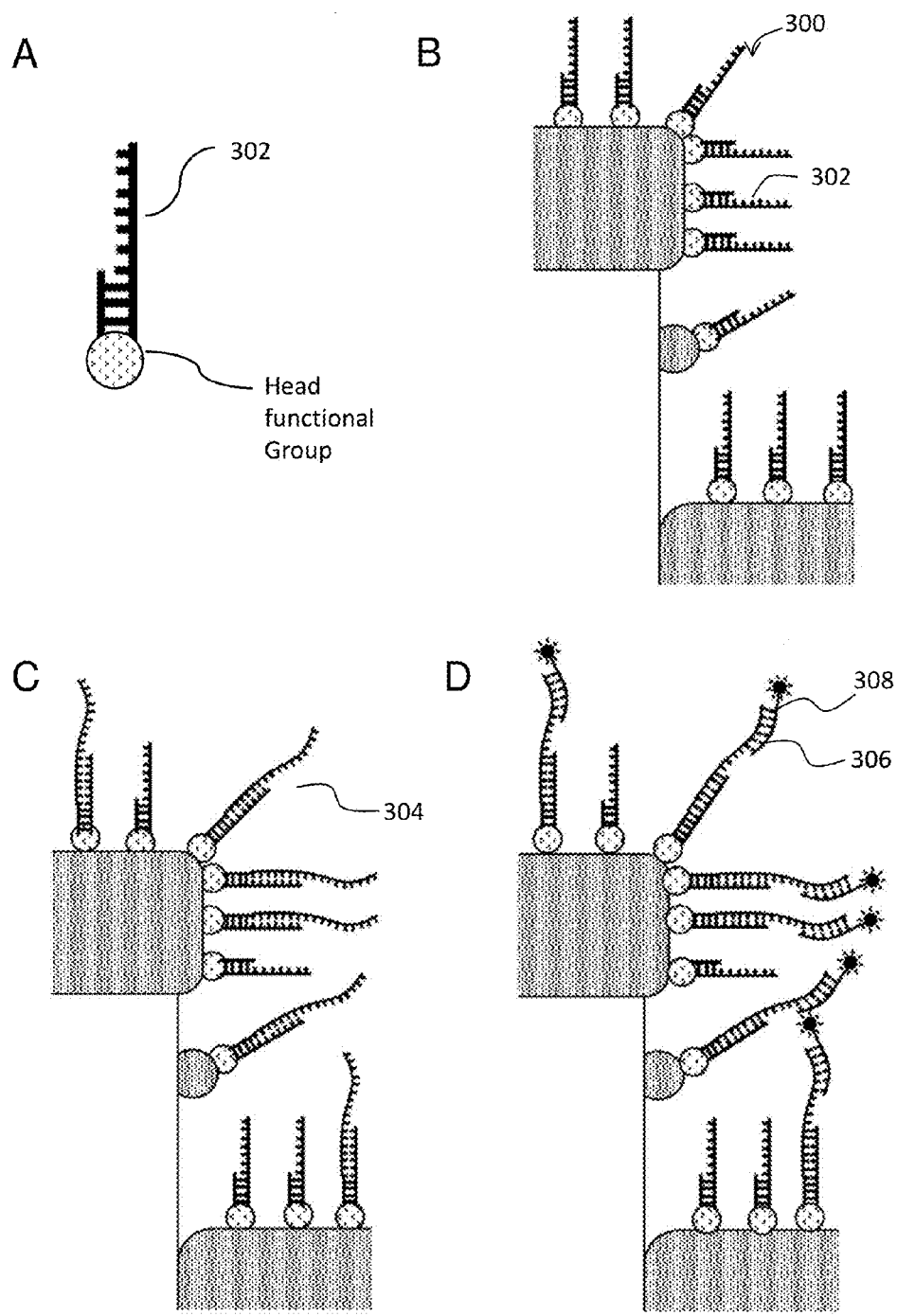
FIG. 6 schematically illustrates another embodiment nucleic acid detection assay.

Some of the steps of an assay are shown in FIGS. 4 and 5. General methods for methods for molecular interactions between capture agents and their binding partners (including analytes) are well known in the art (see, e.g., Harlow et al., *Antibodies: A Laboratory Manual*, First Edition (1988) Cold spring Harbor, N.Y.; Ausubel, et al, *Short Protocols in Molecular Biology*, 3rd ed., Wiley & Sons, 1995). The methods shown in FIGS. 4 and 5 are exemplary; the methods described in those figures are not the only ways of performing an assay.

Some of the steps of an exemplary antibody binding assay are shown in FIG. 4. In this assay, nanodevice 100 is linked to an antibody in accordance with the methods described above to produce a nanosensor 200 that comprises antibodies 202 that are linked to the molecular adhesion layer of the nanodevice. After nanosensor 200 has been produced, the nanosensor is contacted with a sample containing a target analyte (e.g., a target protein) under conditions suitable for specific binding. The antibodies 202 specifically bind to target analyte 204 in the sample. After unbound analytes have been washed from the nanosensor, the nanosensor is contacted with a secondary antibody 206 that is labeled with a light-emitting label 208 under conditions suitable for specific binding. After unbound secondary antibodies have been removed from the nanosensor, the nanosensor may be read to identify and/or quantify the amount of analyte 204 in the initial sample.

Some of the steps of an exemplary nucleic acid binding assay are shown in FIG. 5. In this assay, nanodevice 100 is linked to a nucleic acid, e.g., an oligonucleotide in accordance with the methods described above to produce a nanosensor 300 that comprises nucleic acid molecules 302 that are linked to the molecular adhesion layer. After nanosensor 200 has been produced, the nanosensor is contacted with a sample containing target nucleic acid 304 under conditions suitable for specific hybridization of target nucleic acid 304 to the nucleic acid capture agents 302. Nucleic acid capture agents 304 specifically binds to target nucleic acid 304 in the sample. After unbound nucleic acids have been washed from the nanosensor, the nanosensor is contacted with a secondary nucleic acid 306 that is labeled with a light-emitting label 308 under conditions for specific hybridization. After unbound secondary nucleic acids have been removed from the nanosensor, the nanosensor may be read to identify and/or quantify the amount of nucleic acid 304 in the initial sample.

One example of an enhanced DNA hybridization assay that can be performed using a subject device is a sandwich hybridization assay. The capture DNA is a single strand DNA functioned with thiol at its 3'-end The detection DNA is a single strand DNA functioned with a fluorescence label e.g., IRDye800CW at its 3'-end. Both the capture and detection DNA has a length of 20 bp. They are synthesized with different sequences to form complementary binding to a targeted DNA at different region. First the capture DNA is immobilized on the D2PA nanodevice's metal surface through sulfur-gold reaction. Then targeted DNA is added to the nanodevice to be captured by the capture DNA. Finally the fluorescence labeled detection DNA is added to the nanodevice to detect the immobilized targeted DNA. After washing off the unbound detection DNA, the fluorescence signal emanate from the nanodevices' surface is measured for the detection and quantification of targeted DNA molecules.

In the embodiments shown in FIGS. 4 and 5, bound analyte can be detected using a secondary capture agent (i.e. the "detection agent") may be conjugated to a fluorophore or an enzyme that catalyzes the synthesis of a chromogenic compound that can be detected visually or using an imaging system. In one embodiment, horseradish peroxidase (HRP) may be used, which can convert chromogenic substrates (e.g., TMB, DAB, or ABTS) into colored products, or, alternatively, produce a luminescent product when chemiluminescent substrates are used. In particular embodiments, the light signal produced by the label has a wavelength that is in the range of 300 nm to 900 nm). In certain embodiments, the label may be electrochemiluminescent and, as such, a light signal can be produced by supplying a current to the sensor.

In some embodiments, the secondary capture agent (i.e. the detection agent), e.g., the secondary antibody or secondary nucleic acid, may be linked to a fluorophore, e.g., xanthene dyes, e.g. fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2', 7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy3, and Cy5, IRDye800, IRDye800CW, Alexa 790, Dylight 800, etc.

The primary and secondary capture agents should bind to the target analyte with highly-specific affinity. However, the primary and secondary capture agents cannot be the molecule because they need to bind to different sites in the antigen. One example is the anti-human beta amyloid capture antibody 6E10 and detection G210, in which case 6E10 binds only to the $10^{th}$ amine site on human beta amyloids peptide while G210 binds only to the $40^{th}$ amine site. Capture agent and secondary capture agent do not react to each other. Another example uses rabbit anti-human IgG as capture antibody and donkey anti-human IgG as detection antibody. Since the capture and detection agents are derived from different host species, they do not react with each other.

Methods for labeling proteins, e.g., secondary antibodies, and nucleic acids with fluorophores are well known in the art. Chemiluminescent labels include acridinium esters and sulfonamides, luminol and isoluminol; electrochemiluminescent labels include ruthenium (II) chelates, and others are known.

Applications

The subject methods and compositions find use in a variety applications, where such applications are generally analyte detection applications in which the presence of a particular analyte in a given sample is detected at least qualitatively, if not quantitatively. Protocols for carrying out analyte detection assays are well known to those of skill in the art and need not be described in great detail here. Generally, the sample suspected of comprising an analyte of interest is contacted with the surface of a subject nanosensor under conditions sufficient for the analyte to bind to its respective capture agent that is tethered to the sensor. The capture agent has highly specific affinity for the targeted molecules of interest. This affinity can be antigen-antibody reaction where antibodies bind to specific epitope on the antigen, or a DNA/RNA or DNA/RNA hybridization reaction that is sequence-specific between two or more complementary strands of nucleic acids. Thus, if the analyte of interest is present in the sample, it likely binds to the sensor at the site of the capture agent and a complex is formed on the sensor surface. Namely, the captured analytes are immobilized at the sensor surface. After removing the unbounded analytes, the presence of this binding complex on the surface of the sensor (i.e. the immobilized analytes of interest) is then detected, e.g., using a labeled secondary capture agent.

Specific analyte detection applications of interest include hybridization assays in which the nucleic acid capture agents are employed and protein binding assays in which polypeptides, e.g., antibodies, are employed. In these assays, a sample is first prepared and following sample preparation, the sample is contacted with a subject nanosensor under specific binding conditions, whereby complexes are formed between target nucleic acids or polypeptides (or other molecules) that are complementary to capture agents attached to the sensor surface.

In one embodiment, the capture oligonucleotide is synthesized single strand DNA of 20-100 bases length, that is thiolated at one end. These molecules are are immobilized on the nanodevices' surface to capture the targeted single-strand DNA (which may be at least 50 bp length) that has a sequence that is complementary to the immobilized capture DNA. After the hybridization reaction, a detection single strand DNA (which can be of 20-100 bp in length) whose sequence are complementary to the targeted DNA's unoccupied nucleic acid is added to hybridize with the target. The detection DNA has its one end conjugated to a fluorescence label, whose emission wavelength are within the plasmonic resonance of the nanodevice. Therefore by detecting the fluorescence emission emanate from the nanodevices' surface, the targeted single strand DNA can be accurately detected and quantified. The length for capture and detection DNA determine the melting temperature (nucleotide strands will separate above melting temperature), the extent of mispairing (the longer the strand, the lower the mispairing). One of the concerns of choosing the length for complementary binding depends on the needs to minimize mispairing while keeping the melting temperature as high as possible. In addition, the total length of the hybridization length is determined in order to achieve optimum signal amplification.

A subject sensor may be employed in a method of diagnosing a disease or condition, comprising: (a) obtaining a liquid sample from a patient suspected of having the disease or condition, (b) contacting the sample with a subject nanosensor, wherein the capture agent of the nanosensor specifically binds to a biomarker for the disease and wherein the contacting is done under conditions suitable for specific binding of the biomarker with the capture agent; (c) removing any biomarker that is not bound to the capture agent; and (d) reading a light signal from biomarker that remain bound to the nanosensor, wherein a light signal indicates that the patient has the disease or condition, wherein the method further comprises labeling the biomarker with a light-emitting label, either prior to or after it is bound to the capture agent. As will be described in greater detail below, the patient may suspected of having cancer and the antibody binds to a cancer biomarker. In other embodiments, the patient is suspected of having a neurological disorder and the antibody binds to a biomarker for the neurological disorder.

The applications of the subject sensor include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

The detection can be carried out in various sample matrix, such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

In some embodiments, a subject biosensor can be used diagnose a pathogen infection by detecting a target nucleic acid from a pathogen in a sample. The target nucleic acid may be, for example, from a virus that is selected from the group comprising human immunodeficiency virus 1 and 2 (HIV-1 and HIV-2), human T-cell leukaemia virus and 2 (HTLV-1 and HTLV-2), respiratory syncytial virus (RSV), adenovirus, hepatitis B virus (HBV), hepatitis C virus (HCV), Epstein-Barr virus (EBV), human papillomavirus (HPV), varicella zoster virus (VZV), cytomegalovirus (CMV), herpes-simplex virus 1 and 2 (HSV-1 and HSV-2), human herpesvirus 8 (HHV-8, also known as Kaposi sarcoma herpesvirus) and flaviviruses, including yellow fever virus, dengue virus, Japanese encephalitis virus and West Nile virus. The present invention is not, however, limited to the detection of DNA sequences from the aforementioned viruses, but can be applied without any problem to other pathogens important in veterinary and/or human medicine.

Human papillomaviruses (HPV) are further subdivided on the basis of their DNA sequence homology into more than 70 different types. These types cause different diseases. HPV types 1, 2, 3, 4, 7, 10 and 26-29 cause benign warts. HPV types 5, 8, 9, 12, 14, 15, 17 and 19-25 and 46-50 cause lesions in patients with a weakened immune system. Types 6, 11, 34, 39, 41-44 and 51-55 cause benign acuminate warts on the mucosae of the genital region and of the respiratory tract. HPV types 16 and 18 are of special medical interest, as they cause epithelial dysplasias of the genital mucosa and are associated with a high proportion of the invasive carcinomas of the cervix, vagina, vulva and anal canal. Integration of the DNA of the human papillomavirus is considered to be decisive in the carcinogenesis of cervical cancer. Human papillomaviruses can be detected for example from the DNA sequence of their capsid proteins L1 and L2. Accordingly, the method of the present invention is especially suitable for the detection of DNA sequences of HPV types 16 and/or 18 in tissue samples, for assessing the risk of development of carcinoma.

In some cases, the nanosensor may be employed to detect a biomarker that is present at a low concentration. For example, the nanosensor may be used to detect cancer antigens in a readily accessible bodily fluids (e.g., blood, saliva, urine, tears, etc.), to detect biomarkers for tissue-specific diseases in a readily accessible bodily fluid (e.g., a biomarkers for a neurological disorder (e.g., Alzheimer's antigens)), to detect infections (particularly detection of low titer latent viruses, e.g., HIV), to detect fetal antigens in maternal blood, and for detection of exogenous compounds (e.g., drugs or pollutants) in a subject's bloodstream, for example.

The following table provides a list of protein biomarkers that can be detected using the subject nanosensor (when used in conjunction with an appropriate monoclonal antibody), and their associated diseases. One potential source of the biomarker (e.g., "CSF"; cerebrospinal fluid) is also indicated in the table. In many cases, the subject biosensor can detect those biomarkers in a different bodily fluid to that indicated. For example, biomarkers that are found in CSF can be identified in urine, blood or saliva, for example.

| Marker | disease |
|---|---|
| Aβ42, amyloid beta-protein (CSF) | Alzheimer's disease. |
| fetuin-A (CSF) | multiple sclerosis. |
| tau (CSF) | niemann-pick type C. |

-continued

| Marker | disease |
|---|---|
| secretogranin II (CSF) | bipolar disorder. |
| prion protein (CSF) | Alzheimer disease, prion disease |
| Cytokines (CSF) | HIV-associated neurocognitive disorders |
| Alpha-synuclein (CSF) | parkinsonian disorders (neuordegenerative disorders) |
| tau protein (CSF) | parkinsonian disorders |
| neurofilament light chain (CSF) | axonal degeneration |
| parkin (CSF) | neuordegenerative disorders |
| PTEN induced putative kinase 1 (CSF) | neuordegenerative disorders |
| DJ-1 (CSF) | neuordegenerative disorders |
| leucine-rich repeat kinase 2 (CSF) | neuordegenerative disorders |
| mutated ATP13A2 (CSF) | Kufor-Rakeb disease |
| Apo H (CSF) | parkinson disease (PD) |
| ceruloplasmin (CSF) | PD |
| Peroxisome proliferator-activated receptor gamma coactivator-1 alpha (PGC-1α)(CSF) | PD |
| transthyretin (CSF) | CSF rhinorrhea (nasal surgery samples) |
| Vitamin D-binding Protein (CSF) | Multiple Sclerosis Progression |
| proapoptotic kinase R (PKR) and its phosphorylated PKR (pPKR) (CSF) | AD |
| CXCL13 (CSF) | multiple sclerosis |
| IL-12p40, CXCL13 and IL-8 (CSF) | intrathecal inflammation |
| Dkk-3 (semen) | prostate cancer |
| p14 endocan fragment (blood) | Sepsis: Endocan, specifically secreted by activated-pulmonary vascular endothelial cells, is thought to play a key role in the control of the lung inflammatory reaction. |
| Serum (blood) | neuromyelitis optica |
| ACE2 (blood) | cardiovascular disease |
| autoantibody to CD25 (blood) | early diagnosis of esophageal squamous cell carcinoma |
| hTERT (blood) | lung cancer |
| CAI25 (MUC 16) (blood) | lung cancer |
| VEGF (blood) | lung cancer |
| sIL-2 (blood) | lung cancer |
| Osteopontin (blood) | lung cancer |
| Human epididymis protein 4 (HE4) (blood) | ovarian cancer |
| Alpha-Fetal Protein (blood) | pregnancy |
| Albumin (urine) | diabetics |
| albumin (urine) uria | albuminuria |
| microalbuminuria | kidney leaks |
| AFP (urine) | mirror fetal AFP levels |
| neutrophil gelatinase-associated lipocalin (NGAL) (urine) | Acute kidney injury |
| interleukin 18 (IL-18) (urine) | Acute kidney injury |
| Kidney Injury Molecule-1 (KIM-1) (urine) | Acute kidney injury |
| Liver Fatty Acid Binding Protein (L-FABP) (urine) | Acute kidney injury |
| LMP1 (saliva) | Epstein-Barr virus oncoprotein (nasopharyngeal carcinomas) |
| BARF1 (saliva) | Epstein-Barr virus oncoprotein (nasopharyngeal carcinomas) |
| IL-8 (saliva) | oral cancer biomarker |
| carcinoembryonic antigen (CEA) (saliva) | oral or salivary malignant tumors |
| BRAF, CCNI, EGRF, FGF19, FRS2, GREB1, and LZTS1 (saliva) | Lung cancer |
| alpha-amylase (saliva) | cardiovascular disease |
| carcinoembryonic antigen (saliva) | Malignant tumors of the oral cavity |
| CA 125 (saliva) | Ovarian cancer |
| IL8 (saliva) | spinalcellular carcinoma. |
| thioredoxin (saliva) | spinalcellular carcinoma. |
| beta-2 microglobulin levels - monitor activity of the virus (saliva) | HIV |
| tumor necrosis factor-alpha receptors - monitor activity of the virus (saliva) | HIV |
| CA15-3 (saliva) | breast cancer |

As noted above, a subject nanosensor can be used to detect nucleic acid in a sample. A subject nanosensor may be employed in a variety of drug discovery and research applications in addition to the diagnostic applications described above. For example, a subject nanosensor may be employed in a variety of applications that include, but are not limited to, diagnosis or monitoring of a disease or condition (where the presence of an nucleic acid provides a biomarker for the disease or condition), discovery of drug targets (where, e.g., an nucleic acid is differentially expressed in a disease or condition and may be targeted for drug therapy), drug screening (where the effects of a drug are monitored by assessing the level of an nucleic acid), determining drug susceptibility (where drug susceptibility is associated with a particular profile of nucleic acids) and basic research (where is it desirable to identify the presence a nucleic acid in a sample, or, in certain embodiments, the relative levels of a particular nucleic acids in two or more samples).

In certain embodiments, relative levels of nucleic acids in two or more different nucleic acid samples may be obtained using the above methods, and compared. In these embodiments, the results obtained from the above-described methods are usually normalized to the total amount of nucleic acids in the sample (e.g., constitutive RNAs), and compared. This may be done by comparing ratios, or by any other means. In particular embodiments, the nucleic acid profiles of two or more different samples may be compared to identify nucleic acids that are associated with a particular disease or condition.

In some examples, the different samples may consist of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

Examples

Aspects of the present teachings can be further understood in light of the following examples, which should not be construed as limiting the scope of the present teachings in any way.

The following example provides a description of how fluorescence and detection sensitivity of an immunoassay with Protein A and the human-immunoglobulin G (IgG) tagged with near IR dye (IRDye800CW) was measured using a new plasmonic structure, D2PA, with a self-assembled monolayer (SAM) of molecular spacer. The average fluorescence of the immunoassay on D2PA is enhanced by 7,400 fold, and the detection sensitivity by 3,000,000 fold (the limit of detection is reduced from 0.9 nM to 0.3 fM), compared to identical assays performed on glass plates. Furthermore, the average fluorescence enhancement has a dynamic range of 8 orders of magnitude (from 100 nM to 1 fM), and uniform over the entire large sample area with a spatial variation ±9%. When a single molecule fluorophore is placed at a "hot spot" of D2PA, its fluorescence is enhanced by $4\times10^6$ fold, which indicates the potential to further increase the average enhancements and the detection sensitivity significantly. The observed enhancements are orders of magnitude higher than previously reported. The large enhancements are attributed to the unique 3D architecture of the D2PA that can overcome some key shortcomings in current plasmonic structure design, as well as the use of the thin SAM molecular spacer. It is suspected that D2PA may concentrate biomarkers in a solution into the hot spots of the plasmonic structure, which can further improve the enhancement. The fabrication method of D2PA plates is simple, inexpensive and scalable. Together with good spatial uniformity, wide dynamic range, and ease to manufacture, the giant enhancements in immunoassay's fluorescence and detection sensitivity should have broad applications in biology study, medical diagnosis, and many others.

Materials and Methods I

Plasmonic Structure.

Figure 7:
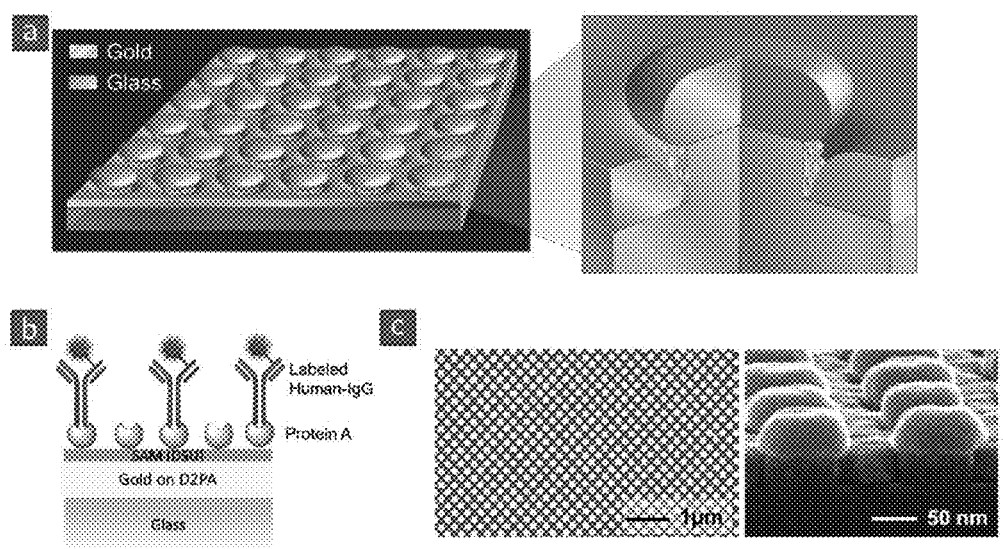
FIG. 7 Disk-coupled dots-on-pillar antenna array (D2PA) plate and immunoassay. (a) Schematic (overview and cross-section) of D2PA plate without an immunoassay. D2PA has an array of dense three-dimensional (3D) resonant cavity nanoantennas (formed by the gold disks on top of periodic nonmetallic pillars and the gold backplane on the pillar foot) with dense plasmonic nanodots inside, and couples the metallic components through nanogaps. (b) Schematic of the immunoassay on the D2PA, consisting of a self-assembled monolayer (SAM) of adhesion layer, Protein-A (as capture layer) and human-IgG pre-labeled with IRDye-800cw (as pre-labeled biomarker). (c) Scanning electron micrograph (SEM) of D2PA with 200 nm period (overview and cross-section). The gold nanodots rested on the silica nano-pillar sidewalls are clearly observed.

The plasmonic architecture described herein will be referred to as "disk-coupled dots-on-pillar antenna array, (D2PA)", has an array of dense three-dimensional (3D) resonant cavity nanoantennas with dense plasmonic nanodots inside and the nanogaps that couple the metallic components (illustrated in FIG. 7; See also Li et al Optics Express 2011 19, 3925-3936). The 3D antennas greatly increase the efficiency in receiving and radiating light, the metallic nanodots and the nanogaps further "focus" the light to small regions to increase local electric fields, and the high densities increase the average enhancement and uniformity. Particularly, the D2PA consists of a periodic non-metallic (e.g. dielectric or semiconductor) pillar array (200 nm pitch, ~100 nm diameter, and ~65 nm height), a metallic disk (~135 nm diameter) on top of each pillar, a metallic backplane on the foot of the pillars, metallic nanodots randomly located on the pillar walls, and nanogaps between these metal components (FIG. 7). The disk array and the backplane (both are 55 nm thick) form a 3D cavity antenna that can efficiently traps the excitation light vertically and laterally. The nanodots have diameters of ~5-20 nm, and the nanogaps between them and the nanodisks are 1-10 nm. Each pillar has about 10 to 50 nanodots depending upon the pillar geometry; and the pillar density is $2.5\times10^9$ pillars/cm$^2$. The exact diameter and height of the pillar and metal disks, which were optimized to match the wavelengths of excitation laser and fluorescence, as well as the roles of each element of D2PA in plasmonic enhancement have been discussed elsewhere (Li et al Optics Express 2011 19, 3925-3936).

The D2PA structures were fabricated on 4" fused silica wafers by a nanofabrication approach that combines nanoimprint (top-down) with self-aligned self-assembly (bottom-up). The pillars were patterned first in the silica wafer by nanoimprint and reactive ion etching. Then a thin gold layer was evaporated onto the wafer in a direction normal to the wafer surface, which simultaneously deposited the gold nanodisk on the pillar top, the gold backplane, and gold nanodots on the pillar sidewall. The gold deposited on the pillar sidewall is much thinner than that on the top of the nanodisks and the backplane. Such thin gold is unstable and diffuses at the elevated evaporation temperature; and together with the non-wetting property of gold on SiO2 surface, the gold self-assembles into nanodots with a small gap in between and self-aligned precisely next to the gold nanodisk. Other details of D2PA structure and fabrication are described elsewhere (Li et al, supra; Chou et al Science 1996 272: 85-87 and Chou et al Applied Physics Letters 1995 67: 3114-3116, which are all incorporated by reference for those teachings).

Figure 20:
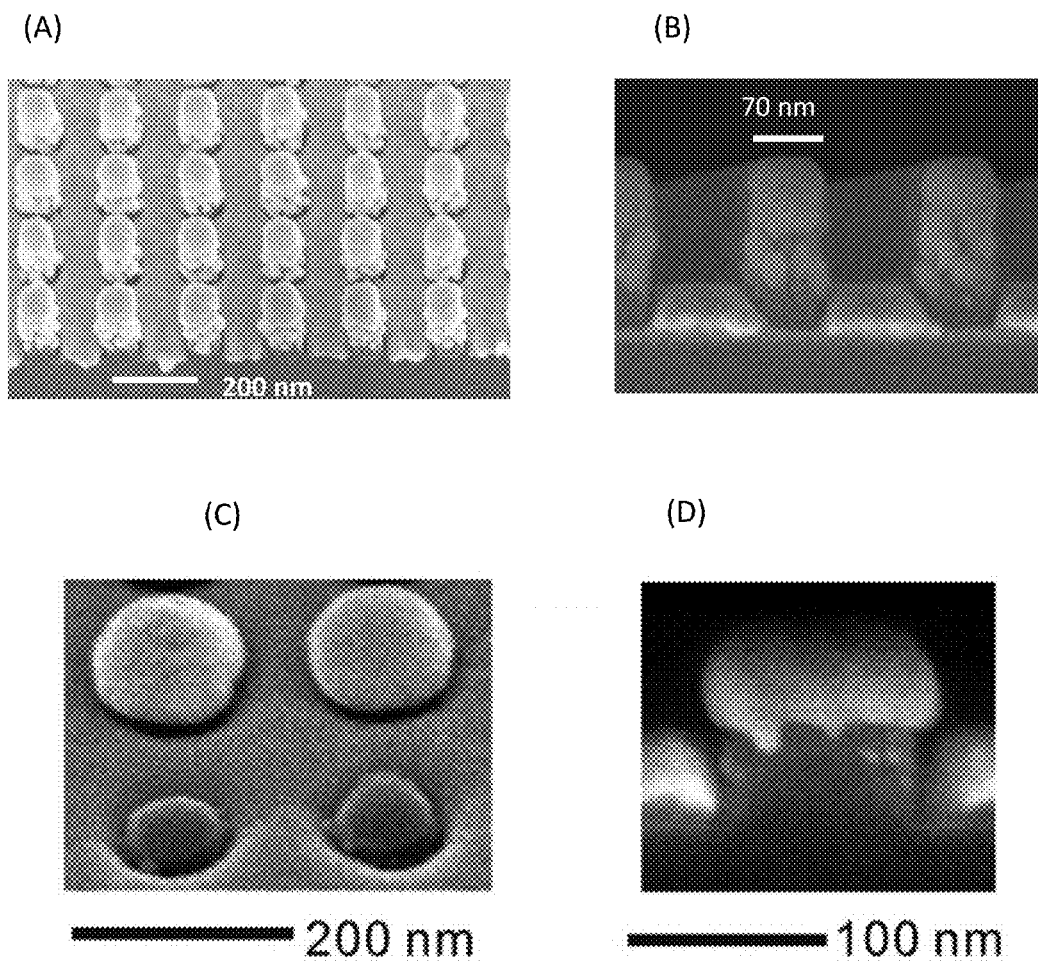
FIG. 20 shows a series of scanning electron micrographs.

FIG. 20 shows scanning electron micrographs of nanodevices—Disk-Coupled Dots-on-Pillar Antenna-Array (D2PA). (A) Top view and (B) side view of the same D2PA with 70 nm diameter metallic disk and metallic dot structure on sidewall of size ranging from 5 nm to 30 nm. And (C) top view and (D) sideview of another D2PA with metallic disk diameter of 100 nm and metallic dot structure on sidewall of size ranging from 1 nm to 15 nm. In (C) two of four disks are missing. Both D2PAs have a period of 200 nm.

Immunoassay, Fluorophores, Adhesion Layer and Reference.

The immunoassay was used to test the enhancement in fluorescence and detection sensitivity was a direct assay of Protein A and human immunoglobulin G (IgG), which has been widely used as the simplest model assay for such testing. Protein-A on a solid plate surface served as the capture agent to capture the IgG (the targeted analyte) in a solution which are already labeled with infrared fluorescent dye (IRDye800CW (Li-COR)), hence there was no need to use additional detection agent. Protein A catch human IgG through the strong Fc (Fragment, crystallizable) binding. The concentration of IgG in solution was then quantified by measuring its fluorescent labels.

Because Protein A does not bind to the metal surface well, for the D2PA plate, an additional adhesion layer was used between the metal and Protein A. This adhesion layer will add an additional material to the spacer, and could, potentially, weaken the plasmonic enhancement. To limit the total spacer thickness while providing good binding of Protein A to the metal (gold in our case), we used a self-assemble-monolayer (SAM) of dithiobis succinimidyl undecanoate (DSU) as the adhesion layer. The DSU molecule has one end of sulfide which strongly binds to a gold surface and the other end of N-hydroxysuccinimide (NHS) ester group which binds well to Protein A's amine group[26]. The SAM was ~1.7 nm thick with refractive index n=1.50. Together with the Protein A layer which is estimated to be 4.8 nm, the total spacer thickness is 6.5 nm.

For comparison with the D2PA plate's immunoassay fluorescence enhancement measurements, we used plain flat glass plates as the reference. The immunoassay on the D2PA plates and the reference was prepared in the same manner and the same batch.

Preparation of Fluorophore Label and Immunoassay.

The human IgG (Rockland Immunochemicals) was labeled with the infrared fluorescent dye, IRDye800CW, in house. NHS ester group on the dye molecule was coupled to the amine group on IgG by mixing the reactive dye with IgG solution and letting them react for 2 hours at 20° C. in dark environment. Free dye was separated through buffer exchange by using desalting spin columns (Pierce Zeba). Each IgG has an average of 1.3 IRdye800CW molecules.

For coating DSU SAM on the D2PA, the plates were immersed in a solution of 0.5 mM DSU (Dojindo, Japan) in 1,4-dioxane (Sigma-Aldrich), and incubated overnight at room temperature in a sealed container to form the SAM spacer. After incubation, they were rinsed extensively in 1,4-dioxane and dried with argon gas and ready for Protein A immobilization.

Protein A (Rockland Immunochemicals) in phosphate buffered saline (PBS) buffer solution (pH=7.4, Sigma-aldrich) was dropped on the D2PA and reference plates, and each plate was incubated in a sealed container for 120 min at room temperature. Then the plates were washed 3 times in wash solution (R&D systems) for 15 minutes each to remove the unbounded molecules. After coating Protein A, we diced the plates into 5 mm×5 mm square pieces for testing. Then fluorescence-labeled IgG in PBS solution were then dropped on the Protein A layer and incubated in a sealed container for 60 min at room temperature. After another washing in the same manner, the plates were gently rinsed in streams of deionized water to remove any salt content. After drying with argon gas, the plates were optically measured immediately.

To precisely control the concentrations of IgG on the plates, we first prepare different concentrations of IgG in PBS solution from 1 µM to 10 aM through serial dilution from stock solution (using dispense pipette with ±0.6% inaccuracy). Then we precisely dropped 3 µL solution of each concentration on individual square pieces (each 5 mm×5 mm). The 3 µL volume is chosen to make sure that the solution layer, after completely wetting the plate top surface, will not spill to the plate's back surface.

Optical Measurements.

The average fluorescence of the immunoassays on the D2PA plates and the reference plates were measured using a commercial laser scanning confocal spectrometer (ARAMIS, Horiba Jobin Yvon) with a 785 nm laser excitation. The system uses a microscope lens to focus the excitation laser beam normally on the sample surface and uses the same lens to collect the generated fluorescence. The laser beam was in a rapid raster-scanning (by a scanning galvo mirror system) to homogenize the excitation over an area, termed "laser scan area", which can be varied from a laser spot size (diffraction limited focal point) up to 100 µm×100 µm. By a step-and-repeat of the laser scan area using an x-y stage, up to 20 mm×20 mm of the sample area can be measured automatically. The optical signals from a sample were sent to a spectrometer which consists of gratings and a CCD for spectrum measurement. Typically, we used a 10× objective (Numerical Aperture (N.A.)=0.25), and 100 µm×100 µm laser scan area. For measuring single molecule fluorescence, another optical set-up that gives 2D maps of optical signal over the excitation area was used.

Results and Discussion I

Figure 8:
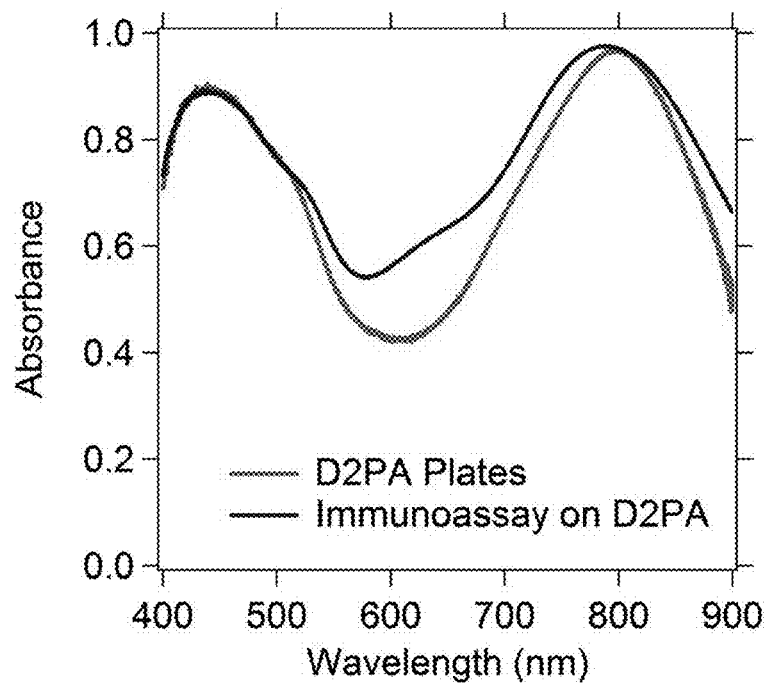
FIG. 8 Measured absorbance spectrum of D2PA with (blue line) and without (red line) the immunoassay being deposited. The peak absorbance is 98% and 97%, and the resonance peak width is 165 nm and 145 nm, respectively, with and without the immunoassay. Deposition of the immunoassay slightly blue-shifted the absorption peak from 795 nm to 788 nm and widened the absorption wavelength range FIG. 9 Measured area-average fluorescence intensity spectrum of the human-IgG labeled with IRDye800CW captured by the assay on the D2PA (red line) and the glass plate (blue line, which is amplified 1000 times to be visible at given scales), respectively. Compared with the assay on the glass plate, the average fluorescence enhancement (dashed line) is 7,440 fold at the peak wavelength of fluorescence (800 nm) and 7,220 fold when average over the FWHM fluorescence. The plasmonic fluorescence enhancement factor (EF) spectrum has much broader FWHM than the fluorescence spectrum, which is consistent with the observed D2PA plasmonic resonance spectrum (FIG. 5).

Plasmonic Resonance of D2PA Plate. The D2PA nanostructure was optimized to make its plasmonic resonance close to the wavelengths of excitation laser (785 nm) as well as the absorption and emission peak of the fluorescent dye (IRDye-800CW) used in the immunoassay (780 nm and 800 nm respectively). Absorbance of the D2PA was obtained by measuring the transmission (T) and reflection (R) spectrum using a white light source, and calibrated to same measurement performed on a glass plate (T=94%) and silver mirror standard (R=98%) respectively. The absorbance (1−T−R) was found to have a resonance peak of 97% at 795 nm and a resonant full width at half maximum (FWHM) of 145 nm for the optimized D2PA plates without any molecular coating. After applying the immunoassay, the peak absorbance becomes 98%, and the resonance peak is blue-shifted slightly to 788 nm, and the FWHM is 165 nm—slightly wider (FIG. 8). A blue-shift, rather than a common red-shift, which was also observed in another plasmonic system, has been attributed to negative molecular polarizability that destructively interferes with the oscillating polarization from the surface plasmon.

Large-Area Average Fluorescence Enhancement over 7,400 Fold with Good Uniformity (±9% Variation). The typical fluorescence spectrum of the Protein A/IgG immunoassay on the D2PA plate and the reference (the flat glass plate) are given in FIG. 9. Both spectra were measured on the assays with 10 nM fluorescent-labeled IgG with a laser scan area of 100 μm×100 μm). The laser power and the detector integration time were 3 μW and 1 second for the D2PA, and 212 μW and 8 second for the reference glass plate; but were normalized in plotting FIG. 9. Compared to the glass reference sample, the immunoassay's fluorescence intensity on the D2PA is significantly enhanced. On the other hand, the fluorescence peak wavelength is the same (800 nm) and the full-width at the half-maximum (FWHM) is nearly the same (~30 nm) as the reference, which are due to the fact that D2PA's plasmonic resonance has its peak optimized at 788 nm and a FWHM of ~165 nm—5 times wider than the dye fluorescence peak, hence making the plasmonic enhancement factor nearly constant over the entire wavelength range of the IRDye800CW fluorescence.

The average fluorescence enhancement of the immunoassay on the D2PA plate over a reference (the glass plate) was obtained by:

$$EF(\lambda) = \frac{I_{fluo.D2PA}(\lambda)}{I_{fluo.REF}(\lambda)} \frac{I_{Exc.REF}}{I_{Exc.D2PA}}, \quad (1)$$

where $I_{Exc.REF}$ and $I_{Exc.D2PA}$ is the intensity of laser excitation, and $I_{Fluo.REF}$ and $I_{Flour.D2PA}$ is the measured average fluorescence intensity for the reference and D2PA plate respectively. Note that we measured the average fluorescence enhancements using the same IgG concentration for both the reference and the D2PA. This is to avoid the errors caused by the effects of different IgG concentrations. Moreover, to ensure the average accuracy, at least, a total of 5 different laser scan areas (each 100 μm×100 μm) over a sample were measured.

Figure 9:
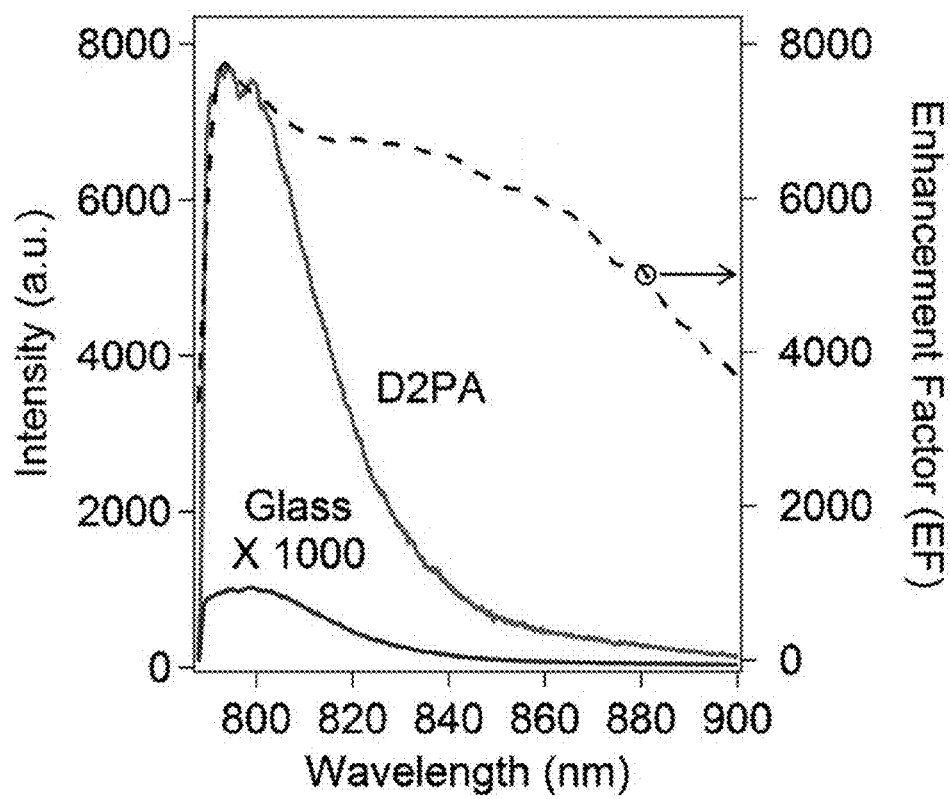

Using the above approach, the measured average fluorescence enhancement of the D2PA plate at 10 nM fluorescent-labeled IgG was 7,440 fold over the reference when the fluorescence peaks are compared, and 7,220 fold when the fluorescence intensities are integrated over the FWHM of the fluorescence spectrum. FIG. 9 shows that the average fluorescence enhancement spectrum has much broader FWHM than the fluorescence spectrum, which is consistent with the observed D2PA plasmonic resonance spectrum (FIG. 8). For 100 nM fluorescent-labeled IgG concentration, the average peak enhancement is 8,460 fold. The immunoassay fluorescence enhancements observed here are two orders of magnitude higher than previous plasmonic enhanced fluorescence in immunoassays (Zhang et al Optics Express 2007 15 2598-2606; Tabakman et al Nature Communications 2011 2: 466).

Figure 10:
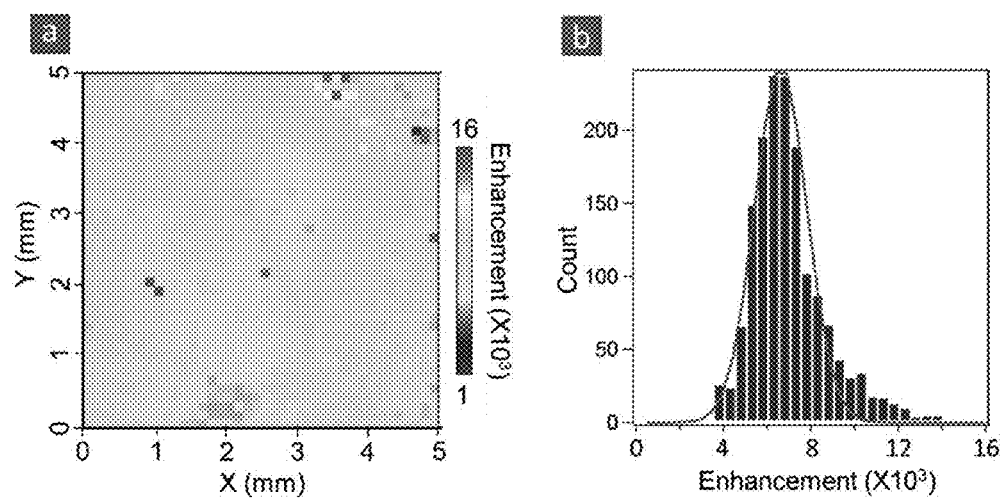
FIG. 10 Measured uniformity of fluorescence enhancement over large area. (a) Measured immunoassay fluorescence enhancement (factor) map over a total 5 mm×5 mm area of the D2PA. The map has total 2,500 tiles (50×50), measured by using each tile area (i.e. laser probe area) of 100 μm×100 μm and a step-and-repeat distance of 100 μm. (b) The corresponding histogram of the measured enhancement factor gives a Gaussian distribution variation of ±9%.

Another important feature of D2PA is the uniformity of the giant average fluorescence enhancement over a large area. The uniformity of D2PA plates was measured by mapping the fluorescence intensities of 10 nM fluorescence-labeled IgG concentration over the entire 5 mm×5 mm area of the D2PA plate. A laser scan area (100 μm×100 μm) was used, termed a "tile" in mapping; hence there are a total 2,500 tiles (50×50) (FIG. 10a). The laser power was 3 μW and the integration time per tile was one second. Statistics performed on the mapping measurements showed that the average fluorescence enhancement over such large sample surface is 7,000 fold with a variation (defined as the variation of a Gaussian distribution) of 18% or ±9% from the mean—very uniform everywhere (FIG. 10b).

For the laser excitation power density and excitation time used in above measurements, we have not observed either saturation or noticeable bleaching, which are essential to ensure accurate enhancement measurements. In fact, the fluorescence signals from both D2PA and the reference samples are found to be linear over a wide range of laser power density and dye concentration, which indicate no saturation. Moreover, the fluorescence vs. time measurement showed that under the laser intensities used, even for a time period much longer than the typical measurement time we used, there is still no noticeable bleaching.

Sub-Femto-Molar Detection Sensitivity and Wide Dynamic Range. In clinical diagnostic applications, the detection sensitivity (i.e. the limit of detection (LoD)) and dynamic range have more practical meaning than the fluorescence enhancement factor. To test these, we measured the immunoassay's fluorescence signals from the D2PA and the reference prepared with different IgG concentrations: from 1 μM to 10 aM (with a series dilution factor of 10). The LoD, determined using the well-accepted standard, is the IgG concentration corresponding to the fluorescence signal that is equal to the background optical noise plus three times of its standard deviation (i.e. the root-mean-squared deviation). In our experiments, the background optical noise were obtained by performing the exactly same optical measurements on a blank sample as the sample with IgG (i.e. the same optical setup, sample area, laser power and integration time). The blank sample was prepared on identical substrates using the same preparation protocol except that the normal step of dropping fluorescent-labeled IgG is replaced by dropping of pure buffer solution (i.e. no IgG).

Figure 11:
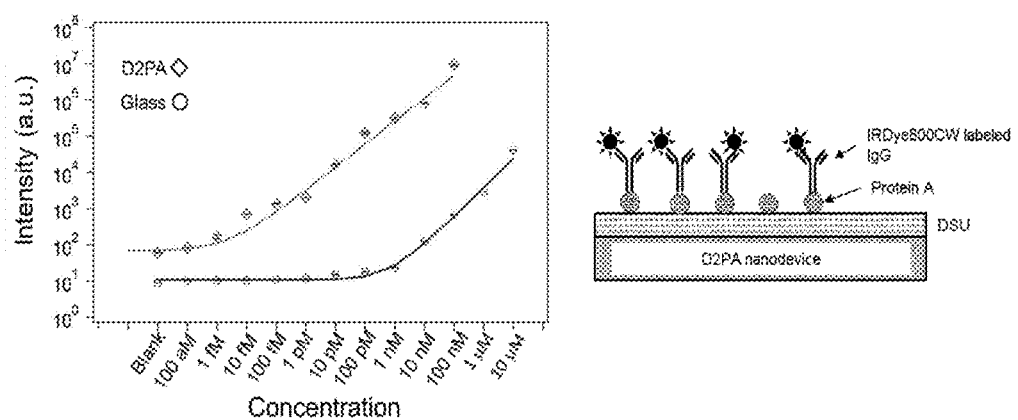
FIG. 11 A model direct assay of protein A and IgG. (A) Fluorescence intensity vs. IgG concentration on D2PA (squares) and glass plate reference (circles). The squares and circles are measured data, and the curves were the fittings using five-parameter logistic regression model to allow an extrapolation of the data points between the measured ones. The limit of detection (LoD) of D2PA and glass plate was found to be 0.3 fM and 0.9 nM, respectively, giving an enhancement of LoD of 3,000,000 fold. (B) Schematic of the immunoassay on the D2PA, consisting of a self-assembled monolayer (SAM) of adhesion layer, Protein-A (as capture layer) and human-IgG pre-labeled with IRDye-800cw (as pre-labeled biomarker).

FIG. 11 shows the logarithm plot of the fluorescence signals versus the fluorescent-labeled IgG concentration deposited on the D2PA and the reference (the response curve). Error bars are the standard deviation, calculated from the measurements at five different sample areas for each concentration. To determine the LoD, we first used five-parameter logistic regression model to create fitting curves which allow an extrapolation of the data points between the measured ones. The LoD of the immunoassay on D2PA plates was found to be 0.3 fM ($3 \times 10^{-16}$ M), and the dynamic range (where the fluorescence is linear with IgG concentration) is over eight (8) orders of magnitude (from 1 μM to 1 fM) (FIG. 11). On the other hand, the LoD of identical immunoassays performed on the reference plates (planar glass plates) was found to be 0.9 nM ($0.9 \times 10^{-9}$ M). Therefore the detection sensitivity is enhanced by 3,000,000 fold (over 6 orders of magnitude) on the D2PA plate compared to the glass plate. This detection sensitivity enhancement is over two orders of magnitude higher than the previous work using plasmonic structures (Zhang et al Optics Express 2007 15 2598-2606; Tabakman et al Nature Communications 2011 2: 466).

Fluorescence Enhancement of Single Molecule Fluorophore at Hot Spot up to $4 \times 10^6$ Fold. To explore the potential in further enhancing fluorescence and detection sensitivity, the fluorescence enhancement of the immunoassay was measured from a single labeled IgG molecule which was placed at a "hot spot" of D2PA (namely the region where the local electric field is the strongest). Such single molecule fluorescence can be visible when the IgG molecules are far apart from each other (i.e. a very low IgG concentration) and a sensitive CCD camera is used.

An IgG concentration of 100 pM was used to study single molecule fluorescence, which gives an average distance between two immobilized IgG about 420 nm. We mapped the two-dimensional fluorescence of the immunoassay using an inverted microscope (Nikon, USA) with 40× objective lens (N.A.=0.6). A 785 nm laser beam was expanded uniformly to illuminate a 50 μm×50 μm area on D2PA plates. Images were continuously collected by an electron multiplying charge-coupled device (EM-CCD, Andor) of 512×512 pixel resolution (hence ~390 nm per pixel for the given laser scanning area). The CCD pixel size oversamples the fluorescence intensity distribution imaged at optical diffraction-limit (0.8 μm determined by Rayleigh criterion).

Figure 12:
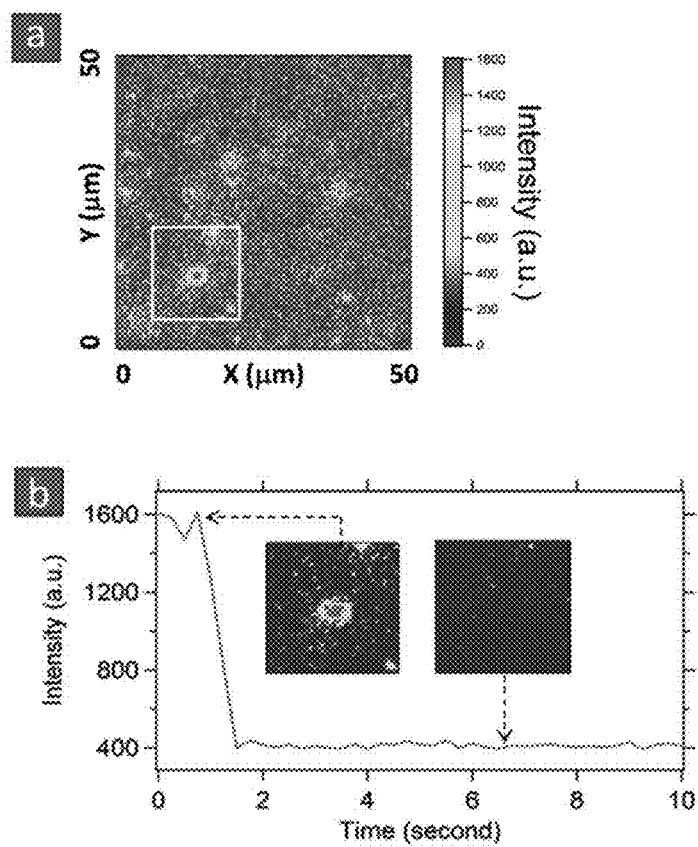
FIG. 12 Single molecule fluorescence of IRDye800CW labeled IgG on D2PA plate. (a) 2D fluorescence image of 50 μm×50 μm area of a Protein A/IgG immunoassay on D2PA plate with an IgG concentration of $10^{-10}$ M. Distinct "bright spots" are visible. And (b) Fluorescence vs. time of a single bright spot. The binary stepwise behavior indicates that the fluorescence is from a single dye molecule placed at a hot spot (large electric field location) of D2PA. Compared with the immunoassay on the glass reference, the single molecule fluorescence at a hot spot is enhanced by $4 \times 10^6$ fold.

From the fluorescence imaging of 100 pM fluorescent-labeled IgG on D2PA plate (FIG. 12a), distinct fluorescence "bright spots" that were randomly distributed in a uniform background were observed. The fluorescence intensity of individual bright spot as a function of time was shown to have a binary stepwise behavior (FIG. 12b), which indicates that a single molecule at or near a D2PA's hot spot first emits fluorescence and then gets bleached.

To estimate the fluorescence enhancement factor for single molecule at a hot spot, $g_{Hotspot}$, we used two methods. For the first method, $g_{Hotspot}$ is the ratio of the single molecule fluorescence signal at a "hot spot" of D2PA, $S_{Hot\ Spot}$, to the average fluorescence signal per molecule on reference sample (which equals to the area-average fluorescence intensity on reference sample, $I_{Ref.Avg}$, divided by the average IgG molecules per unit area on reference sample, $n_{Ref.Avg}$):

$$g_{Hot.Spot} = \frac{S_{Hot.Spot} I_{Exc.Ref}}{(I_{Ref.Avg}/n_{Ref.Avg}) I_{Exc.D2PA}} \quad (2)$$

where $I_{Exc.D2PA}$ and $I_{Exc.Ref}$ is the excitation intensity for the D2PA and reference plates, respectively. According to FIG. 12(a), $S_{Hotspot}$=1,200 counts, $I_{Ref.Avg}$=3,088 counts/μm², and $n_{Ref.Avg}$=7.22×10⁵ molecule/μm², $I_{Ref.Exc}$=1.74 mW and $I_{Exc.D2PA}$=110 μW. We found the fluorescence enhancement is $g_{Hotspot}$=4.4×10⁶, which is 3 orders of magnitude larger than most of the reported fluorescence enhancement for a single molecule in the "hot spot"[31].

For the second method, the average fluorescence intensity per molecule for the reference was deducted from the average fluorescence intensity per molecule for the D2PA plate ($I_{D2PA.Avg}/n_{D2PA.Avg}$) divided by the fluorescence enhancement factor (EF). The division of EF scales the signal from D2PA plate to a regular glass plate:

$$g_{Hot.Spot} = \frac{S_{Hotspot}}{(I_{D2PA.Avg}/n_{D2PA.Avg})/EF}, \quad (3)$$

For $I_{D2PA.Avg}$=19 counts, EF=7,220 and $n_{Avg}$~7.22 molecule/μm², we found $g_{Hotspot}$=3.28×10⁶. Both methods gave consistent results for calculating the single molecule fluorescence enhancements. The average of the two methods gives $g_{Hotspot}$ ~4×10⁶.

Origin of Giant Assay Fluorescence and Detection Sensitivity Enhancement and Uniformity. Without wishing to be bound to any particular theory, it is believed that that there are three primary reasons for the observed enhancement in fluorescence and detection sensitivity. The first and the most important is the unique D2PA plasmonic structure. The second is a proper ultra-thin spacer layer. And the third is the possibility that the D2PA structure might concentrate the biomarkers into the hot spots of the D2PA.

Again without wishing to be bound to any particular theory, it is believed that the plasmonic structure D2PA enhances the fluorescence significantly through four key factors. (1) The 3D antennas array is extremely efficient in receiving excitation light and radiating fluorescent light. As already shown in FIG. 8, the measured absorbance of the optimized D2PA is ~97% at the excitation laser wavelength of 785 nm. A good light absorber is also a good radiator. (2) The small metallic dots and the small gaps in the D2PA can strongly focus light to small regions to significantly enhance local electric fields, as already demonstrated in SERS study (Li et al, supra). The smaller the dots and the gaps, the stronger the focusing (and local electric field enhancements) will be (Schuller et al Nature Materials 2010 9: 193-204 and Nie et al Science 1997 275: 1102-1106). However, it is also well-known that small metallic structures of subwavelength size are extremely poor light absorber and radiator (Fromm et al Nano Letters 2004 4 957-961 and Farahani et al Physical Review Letters 2005 95, article no. 017402). Hence only the small dots and gap alone without antenna will not make a good fluorescence enhancer, since it only can concentrate a small portion of the incoming photons while most of the photons are thrown away, and it cannot efficiently radiate the fluorescence generated in the near field into the far field. (3) The effective coupling between the D2PA's antennas and the nanostructures through the nanogaps between them, making the D2PA effective both in receiving and radiating light and in locally focusing the light to small spots. And (4) the high densities of antennas, dots, and gaps allow larger percentage of targeted molecules to be near the hot spots, hence increasing the fluorescence's average enhancement and uniformity and reducing the performance sensitivity to the device geometry variations. Since the final plasmonic enhancement is a product of all four factors, any plasmonic structures that lacking one of the four factors could end up a poor plasmonic enhancer, which is exactly the problem suffered by the most previous plasmonic structures, and the exact reason why the D2PA, which improves all four factors together, is superior.

To maximize the overall MEF fluorescence, the proper ultra-thin spacer layer plays a key role in balancing the fluorescence excitation and quenching by the same metal. In a separate experiment where the only spacer between a D2PA's metal and a fluorophore is a SiO2 layer (i.e. without any assay), we found that a 5 nm SiO2 thickness offers the best balance between MEF and quenching[30]. Considering the total spacer layer thickness for our D2PA's assay is 6.5 nm (does not include IgG) and the effective permittivity is 3, this spacer has a total effective dielectric distance very close to the 5 nm SiO2 spacer. Therefore, the choice of self-assembled adhesion layer, DSU, offers a proper spacing for MEF.

That theory the D2PA structure may concentrate the biomarkers (targeted analytes) in a solution into the hot spots (i.e. large local electric field region) is just a speculation. Three possible reasons may account for such concentration. (1) The drying of liquid on D2PA surface will occur first outside pillar sidewall, but the last inside the gaps. Hence the liquid movement during the drying may bring biomarkers from other locations into the gaps. (2) The local built-in electric field in D2PA could moves biomarkers (if they are polar molecules) to hot spots. And (3) the SAM adhesion layer, DSU, adheres only the gold not the SiO2, which could led to more Protein A and hence more fluorescent-labeled IgG on gold nanodots than the SiO2 sidewalls that are not covered by the gold.

There are two more important experimental facts that need discussions. (1) The measured immunoassay fluorescence signal intensity does not drop as fast as the biomakers' concentration (i.e. not in 1:1 ratio). This, known to the fluorescence immunoassays, is believed to be caused by the fact that the bonding of IgG to Protein A during the incubation and the loss of the IgG bonded on Protein A during the washing may be different for different IgG concentrations. And (2) the detection sensitivity (LoD) enhancement by D2PA (3,000,000) is over 400 times higher than the fluorescence enhancement (7,400) at 10 nM fluorescent-labeled IgG. We suspect this might be due to biomarkers in a solution being concentrated into the hot spots of D2PA.

It should also be pointed out that the fluorescence enhancement by plasmonic structures is known to depend on the intrinsic quantum efficient (QE) of a dye: stronger enhancement for a lower QE. At a low QE, the fluorescence enhancement is inversely proportional to the QE. The IRDye800cw dye has a quantum efficiency of 7%, similar to the QE of the dyes used in other assay experiments. Even when the difference of the different dyes's QEs is scaled, the observed average fluorescence enhancements are still two orders of magnitude higher than previous experiments.

Finally, the large fluorescence enhancement factor of single fluorophore at a hot spot may indicate that one might be able to further increase the assay detection sensitivity significantly if biomarkers are placed into the hot spots.

Materials and Methods II

Ultrasensitive Detection of Prostate Specific Antigen Preparation of PSA Immunoassay on Nanosensor (Also Termed: D2PA Plate)

The D2PA immunoassay plate is made up of two components: (1) the aforementioned D2PA plasmonic nanostructure and (2) a mixed self-assembled layers of Protein A layer on top of ithiobis succinimidyl undecanoate (DSU). The DSU molecules provide strong cross-link of protein A to gold surface by providing one end of sulfide that strongly binds to gold and the other end of N-hydroxysuccinimide (NHS) ester group that binds well to Protein A's amine group. These molecular layers (Protein A and DSU) have two functions: (1) with a combined thickness of 6.5 nm they will act as a spacer layer that can suppresses metal's fluorescence quenching effect and (2) Since antibodies will bind to protein A through their Fc region, the molecule layers on D2PA can increase the quality of antibody orientation and immobilization, which will further improve the capture efficiency of the antibodies.

For coating DSU SAM and Protein A on the D2PA, freshly fabricated D2PA substrate was first diced into 5 mm×5 mm pieces and immersed in a solution of 0.5 mM DSU (Dojindo, Japan) in 1,4-dioxane (Sigma-Aldrich), and incubated overnight at room temperature in a sealed container. After incubation, the D2PA substrates were rinsed extensively in 1,4-dioxane and dried with argon gas. We immediately place these DSU coated D2PA substrates in separated wells of a standard 96-well plates (Pierce, USA). They were then immersed in 100 uL of 10 ug/mL Protein A (Rockland Immunochemicals) in phosphate buffered saline (PBS) solution (pH=7.2, Sigma-Aldrich) and incubated in a sealed condition overnight in the fridge at 4 C. The solution is then aspirated and each individual D2PA plates is washed 3 times in washing solution (R&D systems) for 15 minutes each to remove the unbonded protein A. The plates were then gently rinsed in streams of deionized water to remove any salt content. After drying with argon gas, the D2PA immunoassay plate was ready for immediate immunoassay testing or stored at −20 C degree for later use.

A fluorescence-based sandwich assay of PSA, which is widely used in both research and clinical diagnosis, was performed on the D2PA immunoassay plates. Capture antibodies (mouse anti-human Kallikrein 3) were first immobilized by immersing the D2PA immunoassay plate in 100 uL of capture antibody solution with concentration of 180 ug/mL and incubate for 2 hours at room temperature. We then aspirate the solution and wash the plates with wash buffer, followed with blocking of each individual plate by immersing in 100 uL of blocking solution (R&D systems) and incubate at room temperature for 1 hour. After the same aspiration/wash process, the D2PA plates in each well were then immersed in 100 uL of PSA (R&D systems) in PBS solution at concentrations from 10 aM to 10 pM with a dilution factor of 10. They were then incubated at room temperature for 2 hours. After another washing, 100 uL of detection antibody (goat anti-human Kallikrein 3) at concentration of 200 ng/mL was added to each individual plate and incubated at room temperature for 1 hour. We then repeated the aspiration/wash process again and added 50 uL of diluted IRDye800CW labeled streptavidin at 50 ng/mL concentration (Rockland Immunochemicals) to each D2PA plate and incubate at room temperature for 1 hour. After the final washing, the D2PA plates were rinsed gently in deionized water and dried with argon gas. The plates were optically measured immediately after the immunoassay was developed.

For comparison with the D2PA immunoassay plates' fluorescence enhancement and sensitivity improvement, we used plain flat glass plates coated with Protein A as the reference. Identical Sandwich PSA immunoassay was prepared on the reference using the reagent from the same batch and treated in the same manner.

Optical Measurements.

Fluorescence-based PSA immunoassays on the D2PA plates and the reference plates were both measured using a commercial laser scanning confocal spectrometer (ARAMIS, Horiba Jobin Yvon) with a 785 nm laser excitation. Excitation light and fluorescence signals were measured above the sample surface at normal angle. The system uses the same microscope lens to focus the excitation laser beam as well as to collect the generated fluorescence light. The laser beam was in a rapid raster-scanning (by a scanning galvo mirror system) to homogenize the excitation over an area, termed "laser scan area", which can be varied from a laser spot size (diffraction limited focal point) up to 100 µm×100 µm. By a step-and-repeat of the laser scan area using an x-y stage, up to 20 mm×20 mm of the sample area can be measured automatically. Fluorescence signals from the sample were coupled to a spectrometer that consists of gratings and a CCD for spectrum measurement. In this report, we used a 10× objective (Numerical Aperture (N.A.)=0.25), and 100 μm×100 μm laser scan area and measured over the entire 5 mm×5 mm D2PA immunoassay plates surface.

Results II

Giant Fluorescence Enhancement Over 1,700 Fold Over Large Area with Good Uniformity (±10% Variation).

Figure 13:
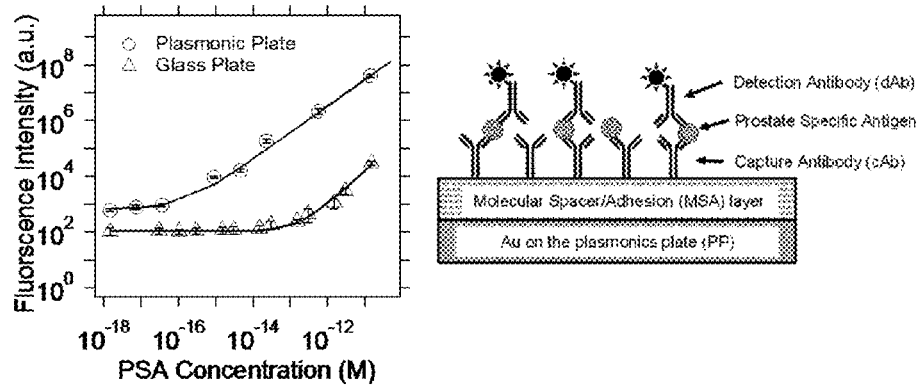
FIG. 13. PSA immunoassay on D2PA plates. The experiment data was fitted using 5-parameter logstic model (solid curve) in order to calculate the LoD. An LoD~10 aM was achieved on D2PA. Compared to glass plates, whose LoD was 0.9 pM, the sensitivity of D2PA is 90,000 folds better. (Chou Group, to be published)

FIG. 13 shows the typical fluorescence spectrum of a PSA immunoassay measured on D2PA plates and the glass plate references. Both spectra were obtained on the assay with 10 pM PSA concentration. The laser power and detector integration time were 3 uW and 10 second for the D2PA, and 212 uW and 8 second for the reference glass plate. We had to use larger laser excitation power for the measurements on reference glass plate in order to get spectrum with good Signal-to-noise ratio (SNR). For the laser excitation power density and excitation time used in above measurements, we have observed neither saturation nor noticeable bleaching, which is essential for the accurate enhancement factor measurements. In fact, the fluorescence signal intensity was constant over a long period of time due to the raster scanning of laser focal spot—bleaching effect is thus minimized in our experiments.

The enhancement factor estimated here still hold for higher concentrations. Using the above approach, the measured average fluorescence enhancement of the D2PA plate at 10 pM PSA was 1,700 fold over the glass reference plate when the fluorescence peak intensities are compared.

Ten Atto-Molar Detection Sensitivity and Wide Dynamic Range.

In order to demonstrate how the giant fluorescence enhancement will improve the immunoassay sensitivity, i.e. LoD, and dynamic range, we measured the PSA immunoassay's fluorescence signals response of PSA concentration from 10 aM to 10 pM (with series dilution factor of 10) on the D2PA and the reference glass plate. The LoD, determined using the well-accepted standard, is the PSA concentration corresponding to the fluorescence signal that is equal to the background optical noise plus three times of its standard deviation (i.e. the root-mean-squared deviation). In PSA immunoassay, the background optical noises were obtained by performing the exactly same optical measurement on an assay during which the PSA solution is replaced by pure PBS buffer solution (i.e. no PSA), while the other steps of preparation protocol remain the same.

FIG. 13 shows the D2PA and reference glass plate's fluorescence immunoassay signals as a function of PSA concentration in logarithm scale (i.e. the response curve). Error bars are the standard deviation calculated from the measurements on five replicates (different sample plates with identical immunoassay and same PSA concentration). We used a five-parameter logistic regression function to create fitting curves, which allow an extrapolation of the data points between the measured PSA concentrations. We then determined the LoD of the immunoassay on D2PA plates to be 10 aM (0.3 fg/mL), and the dynamic range over 6 decades (from 1 fM to 1 uM). We also found the LoD of identical immunoassay performed on the reference glass plates to be 0.9 pM (27 pg/mL). Therefore, the D2PA immunoassay plate's detection sensitivity was enhanced by 90,000 fold compared to the glass plate. In addition, the detection sensitivity we reported here is at least 30 times better than previous reports using competitive techniques.

Ultra-sensitive Detection of Breast Cancer Biomarkers CEA and CA15.3

The nanosensor described above has demonstrated (a) LoD of Carcinoembryonic Antigen (CEA) (see FIG. 14) and CA15.3 (breast cancer biomarkers) (see FIG. 15) of 28 aM (~0.8 fg/mL) and 0.001 U/mL respectively, which is 3~5 orders of magnitude better than commercial ELISA kits (CEA: R&D systems and CA15.3: Abcam), and 5~6 orders of magnitude more sensitive than the clinical cut-off level (4 ng/mL for CEA and 25 U/mL for CA15.3 in blood plasma). (b) both new assays have a linearity of 8 dynamic orders.

Figure 14:
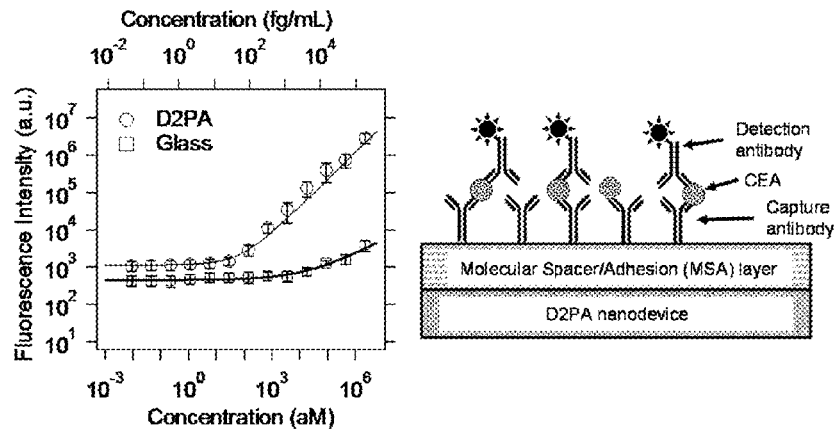
FIG. 14 CEA immunoassay on D2PA plates. Similar configuration is used as the PSA immunoassay. For the tentative trial so far, we managed to achieve an LoD~28aM. Better sensitivity (lower LoD) is expected once we manage to raise the signal to noise ratio. (Chou Group, to be published)
Figure 15:
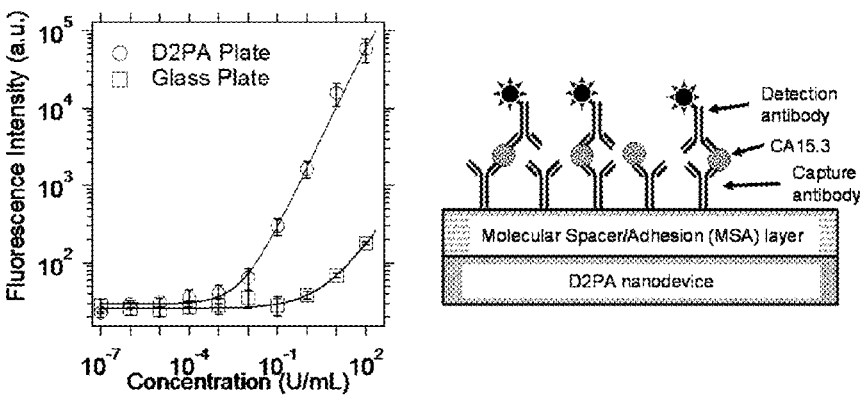
FIG. 15 CA15.3 immunoassay on D2PA plates. A similar configuration is used as the PSA immunoassay. For the tentative trial so far, we managed to achieve an LoD~0.01 U/mL. Better sensitivity (lower LoD) is expected once we manage to raise the signal to noise ratio. (Chou Group, to be published)

For the modified three-layer-sandwich CEA assays on the D2PA plate, we have achieved an LoD of 28 aM (~0.8 fg/mL) in buffer with 8 order dynamic range, respectively, when using a conventional plate reader (area-averaged fluorescence intensity) (FIG. 14). The new assay's LoDs are 170,000-fold better than an identical assay performed on a standard glass plate; 20-fold more sensitive than the current best CEA immunoassays (e.g. random gold island); and 5~6 orders of magnitude more sensitive than the typical CEA level in blood plasma (4 ng/mL).

For CA15.3 Immunoassay, we have achieved an LoD of 0.001 U/mL (unit/mL, 1 unit is an arbitatry value related to a maintained reference antigen preparation. A conversion between U/mL to molarity is not available) and 4~5 orders of magnitude more sensitive than typical CA15.3 level in blood plasma (25 U/mL).

Ultra-Sensitive Detection of Alzheimer's Disease Biomarkers Beta Amyloid 1-40 and 1-42

Figure 16:
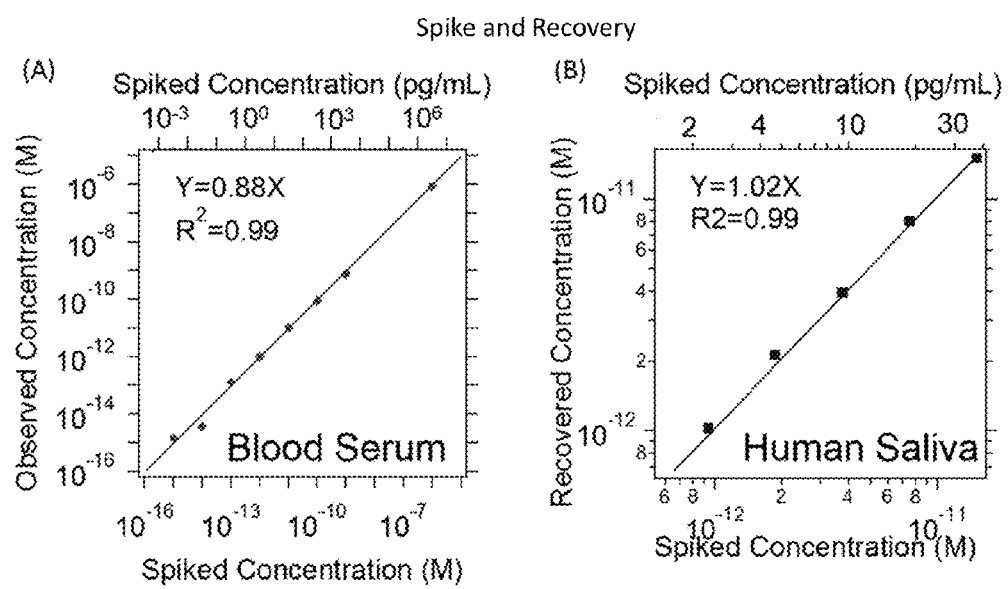
FIG. 16 is two graphs showing the correlation between spiked concentration and observed concentration.

The new assay has demonstrated (a) LoD of β-amyloid (Aβ) in buffer of 2.3 fM (10.3 fg/mL) for Aβ 42 and 0.2 fM (0.9 fg/mL) for Aβ 40; (b) a linearity of over 8 dynamic order, (c) a recovery rate of 88% and 106.8% for serum and saliva spike-and-recovery assessment respectively, (d) 0.06% cross reactivity of Aβ40 over 42 (for 1 pg/ML Aβ42 conc.), and (e) consistent and repeatable detection of Aβ 42 in both blood and saliva. See FIGS. 16 and 17.

In the detecting Aβ-42, the bottom of an ordinary 96 well-plate is replaced with the new assay plate; and commercial "Aβ-42 and 40 ELISA kits" (Covance USA) were modified, where we only attach commercial streptavidin-conjugated fluorescence (IRDye800CW) labels (Rockland USA) to Covance's biotinylated detection antibody (agent) through biotin-avidin reaction (no enzyme was used in our assay). We then used the rest of the kit as is, and followed the conventional protocol. The capture and detection agent in the Covance kit is, respectively, 6E10 and anti-Aβ42 for Aβ-42 and 6E10 and anti-Aβ40 for Aβ-40.

The one that we used for Aβ assay is a bilayer of dithiobis (succinimidyl undecanoate) (DSU) and Protein A. DSU has one end of sulfide which strongly binds to the gold surface on D2PA and the other end of N-hydroxysuccinimide (NHS) ester group which binds well to the amine-group on Protein A, which, in turn, binds to the capture antibody through the Fc region.

(a) Sub-100 fM Limit of Detection (LoD) with 8 Order Dynamic Range.

In the first test on the D2PA plate, we used a two layer model immunoassay of Protein A and fluorescence labeled IgG, and achieved LoD enhancement over a glass plate by more than one million times (×10^6). See FIG. 11. For the modified three-layer-sandwich Aβ assays on the D2PA plate, we have achieved an LoD of 2.3 fM (10.3 fg/mL) and 0.2 fM (0.9 fg/mL) for detecting Aβ 42 and 40 in buffer with 8 order dynamic range, respectively, when using a conventional plate reader (area-averaged fluorescence intensity). The new assay's LoDs are 5,000-fold better than an identical assay performed on a standard glass plate; 500 times more sensitive than the current best commercial Aβ assays (e.g. Meso Scale Discovery); and ~4 and 5 orders of magnitude more sensitive than the typical level Aβ-42 and 40 in blood plasma ($C_{A\beta42}$~50 pg/mL, $C_{A\beta40}$~200 pg/mL), and ~3 and 4 orders of magnitude more sensitive saliva ($C_{A\beta42}$~5 pg/mL and $C_{A\beta40}$~25 pg/mL) respectively.

(b) Excellent Linearity of 8 dynamic orders has been achieved in all tests (See, e.g., FIG. 11).

(c) Recovery rate of 88% for blood serum and 102% for human saliva are achieved in the performed spike-and-recovery test for the Aβ-42 immunoassay on D2PA plate. (See, e.g., FIG. 16)

Figure 17:
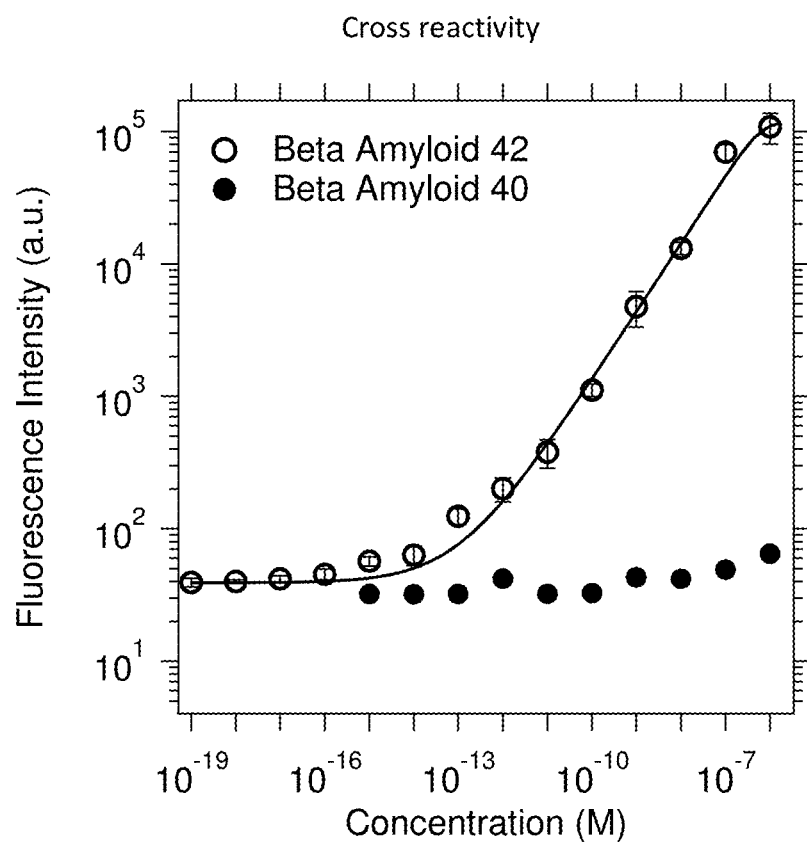
FIG. 17 is two graphs showing the crossreactivity between two antibodies.

(d) Cross-Reactivity of 0.06% of Aβ 42 immunoassay over Aβ 40 at 1 pg/mL Aβ concentration and much better cross-reactivity at a higher Aβ concentration have been achieved (FIG. 17)

Figure 18:
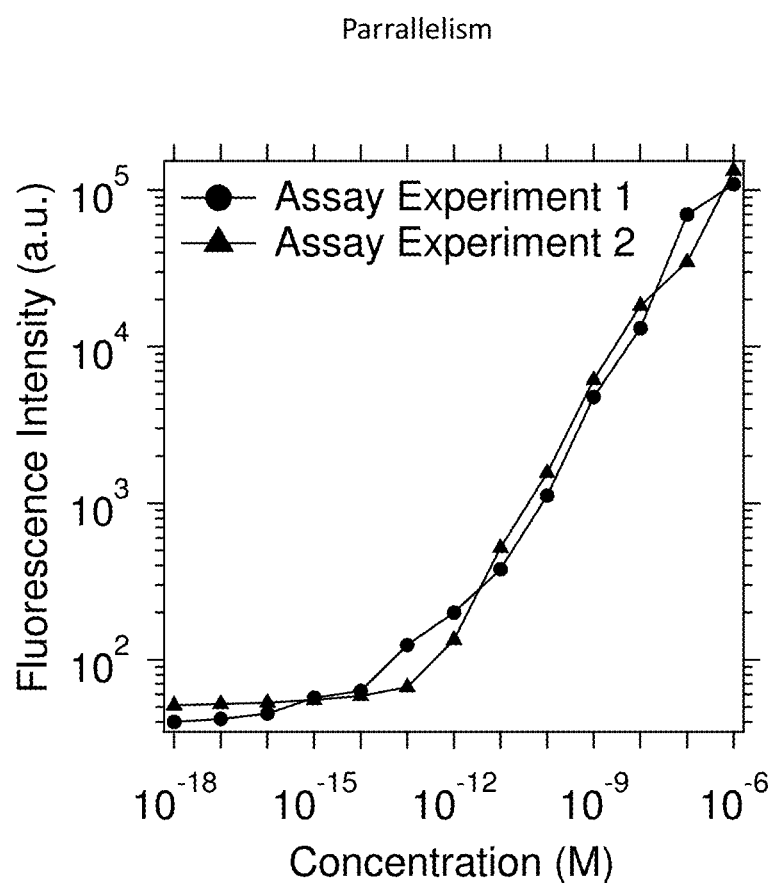
FIG. 18 is two graphs showing reproducibility of results.

(e) Excellent Parallelisms for Aβ immunoassays on D2PA plate (FIG. 18) and other assays on D2PA have been demonstrated. In fact, we have made 2 independent production runs and achieved consistent results.

Ultra-Sensitive DNA Hybridization Assay

One of the example for enhanced DNA hybridization assay using D2PA nanodevice is a sandwich hybridization assay. The capture DNA is a single strand DNA functioned with thiol at its 5'-end (3'-GAAGAAGATAGACTTACATG-5'-SH) (SEQ ID NO:1). The detection DNA is a single strand DNA functioned with a fluorescence label e.g., IRDye800CW at its 3'-end (IR800-3'-TTTGGCTTGTGG TAGTTAGA-5') (SEQ ID NO:2. Both the capture and detection DNA has a length of 20 bp. They are synthesized with different sequences to form complementary binding to a targeted DNA at different region. The targeted DNA is 5'-ACCGAACACCATCAATCTCTTCTATCTGAATG-TACTTTTT-3') (SEQ ID NO:3).

First the capture DNA is immobilized on the D2PA nanodevice's metal surface by incubating the D2PA nanodevice with 5 μM DNA solution diluted with 1×TE buffer with 1M NaCl concentration. Then targeted DNA is diluted in DNA hybridization buffer (H7140, Sigma-Aldrich) and added to the nanodevice to hybridize with the capture DNA. The temperature for hybridization is controlled below the melting temperature at 35° C. Finally the fluorescence labeled detection DNA with concentration of 100 μM is added to the nanodevice to hybridize with the immobilized targeted DNA. The hybridization buffer and temperature remain the same as the last step. After washing off the unbound detection DNA, the fluorescence signal emanate from the nanodevices' surface is measured for the detection and quantification of targeted DNA molecules.

Figure 19:
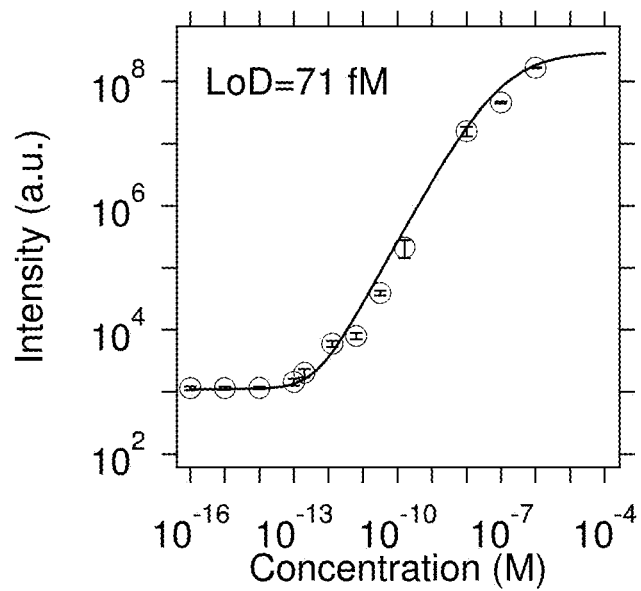
FIG. 19 shows the results of a DNA hybridization assay, and a schematic illustration of the same.
Figure 19:
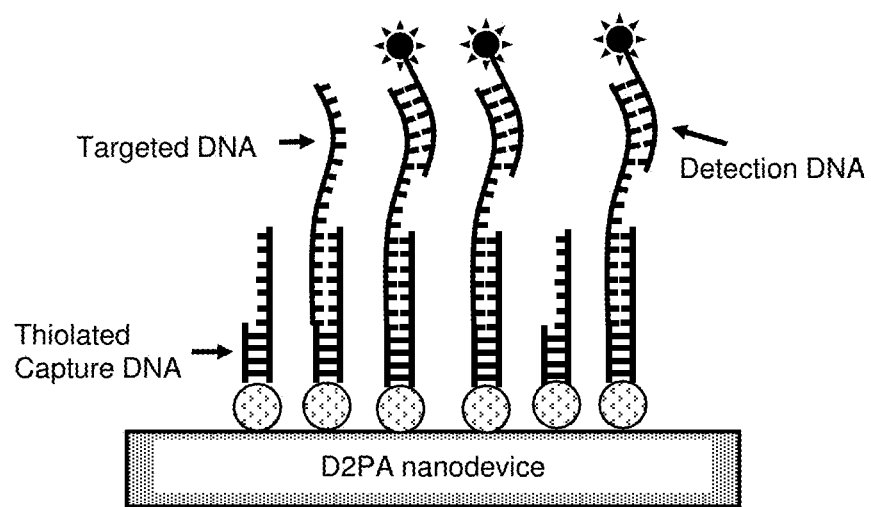

We measured the fluorescence signal intensity from the DNA hybridization assay with different concentrations of targeted DNA. FIG. 19 shows the fluorescence response curve (standard curve) for the hybridization assay performed on D2PA nanodevices. The limit of detection, calculated as the background signal plus three times of the standard deviation of background signal, is 71 fM.

---

What is claimed is:

1. A system for diagnosing a disease or condition, comprising:
(a) a nanosensor that amplifies a light signal comprising:
(i) a substrate; and
(ii) one or a plurality of dielectric or semiconductor pillars extending from a surface of said substrate, wherein each pillar comprises:
a metallic disc on top of the pillar;
a metallic back plane at the foot of the pillar, said metallic back plane covering a substantial portion of said substrate surface near the foot of the pillar;
a metallic dot structure on the sidewall of the pillar; and
a capture agent attached to a part of said metallic dot structure, said metallic disc, said metallic back plane, or said pillar sidewall, either (a) directly or (b) through a molecular adhesion layer, wherein said capture agent specifically binds to a biomarker for said disease or condition;
wherein the molecular adhesion layer determines the space between (i) a label that is directly or indirectly attached to the biomarker and proximal to a surface of the device and (ii) a surface of said metallic dot structure, said metallic disc, said metallic back plane, or said pillar sidewall
wherein the plasmonic resonance of the nanosensor is tuned to cover the absorption peak and/or the emission peak of the label and/or the wavelength of a laser; and
(b) a reader for reading a light signal from said nanosensor, wherein said light signal detects and/or quantifies said biomarker in said sample and provides a diagnosis of said disease or condition.

2. The system of claim 1, wherein said molecular adhesion layer comprises a self-assembled monolayer (SAM) of cross-link molecules, a multi-molecular layers thin film, or a combination thereof.

3. The system of claim 2, wherein said molecular adhesion layer comprise reactive groups that have a high affinity to said capture agent and reactive groups that have high affinity to said metallic dot structure, said metallic disc, said metallic back plane, or said pillar sidewall.

4. The system of claim 2, wherein the exterior surface of said molecular adhesion layer comprises a capture agent-reactive group, selected from an N-hydroxysuccinimidyl ester group, a sulfo-N-hydroxysuccinimidyl ester group, a halo-substituted phenol ester group, a pentafluorophenol ester group, a nitro-substituted phenol ester group, a biotin group, an avidin group, streptavidin, a nucleic acid, an anhydride, an isocyanate, an isothiocyanate, an imidoester, a maleimide, an iodoacetyl, a hydrazide, an aldehyde, or an epoxide.

5. The system of claim 1, wherein said biomarker is labeled with a light-emitting label or an optical detectable label, directly or indirectly, either prior to or after it is bound to said capture agent.

6. The system of claim 5, wherein said label are dye molecules or quantum dots.

7. The system of claim 1, wherein said biomarker is a protein.

8. The system of claim 1, wherein said biomarker is a nucleic acid.

9. The system of claim 1, wherein said biomarker is a molecule or a chemical compound.

10. The system of claim 1, wherein said capture agent is a protein or nucleic acid.

11. The system of claim 1, wherein said capture agent is an agent that binds to said biomarker through an interaction that is sufficient to permit the agent to bind and concentrate the biomarker from a heterogeneous mixture of different molecules.

12. The system of claim 1, wherein said light signal is fluorescence, electroluminescence, chemiluminescence, or other luminescence.

13. The system of claim 1, wherein said light signal is surface enhanced Raman scattering.

14. The system of claim 1, wherein said sample comprises whole blood, fractionated blood, plasma, or serum.

15. The system of claim 1, wherein said sample comprises saliva.

16. The system of claim 1, wherein said sample comprises amniotic fluid, aqueous humour, vitreous humour, breast milk, cerebrospinal fluid (CSF), cerumen (earwax), chyle, chime, endolymph, perilymph, feces, gastric acid, gastric juice, lymph, mucus, nasal drainage, phlegm, pericardial fluid, peritoneal fluid, pleural fluid, pus, rheum, sebum, semen, sputum, sweat, synovial fluid, tears, vomit, urine or exhaled condensate.

17. The system of claim 1, wherein said patient is suspected of having cancer and said capture agent binds to a cancer biomarker.

18. The system of claim 1, wherein said patient is suspected of having a cardiovascular disease, and said capture agent binds to a biomarker for said cardiovascular disease.

19. The system of claim 1, wherein said patient is suspected of having an infectious disease and said capture agent binds to a biomarker for said infectious disease.

20. The system of claim 1, wherein said patient is suspected of having a parasitic disease, an injury, a mental disorder, a neurological disorder, a neuropsychiatric disorder, or an organic disease; and said capture agent binds to a biomarker for said parasitic disease, injury, mental disorder, neurological disorder, neuropsychiatric disorder, or organic disease.

21. The system of claim 1, wherein:
said pillar has a height in the range from 5 nm to 7000 nm;
said metallic disk has a lateral dimension in the range from 4 nm to 1500 nm;
said metallic disk has a vertical thickness in the range from 1 nm to 500 nm;
said back plane has a vertical thickness in the range from 1 nm to 2000 nm;
said metallic dot structure has a diameter in the range from 3 nm to 30 nm; and
said metallic dot structure and said metallic disk on said pillar are spaced by a distance in the range from 0.5 nm to 600 nm; and
the pillars in said plurality of pillars are spaced by a distance in the range from 2 nm to 4000 nm.

22. The system of claim 1, wherein
said pillar comprises a non-metallic material,
the height of said pillar is in the range of 5 nm to less than 130 nm; and
the spacing between pillars in said plurality of pillars is in the range from 2 nm to less than 200 nm.

23. The system of claim 1, wherein said metallic disc and the metallic back plane are spaced by a distance in the range of 0.1 nm to 60 nm.

24. The system of claim 1, wherein top of said at least one pillar has an approximate shape selected from the group of shapes consisting of round, polygonal, pyramidal, elliptical, and elongated bar shaped, and any combination thereof.

25. The system of claim 1, wherein said metallic back plane does not have a hole under each of said pillars, such that said pillars are formed directly on the back plane material.

26. The system of claim 1, wherein said metallic disc, said metallic back plane, and said metallic dots are formed in a single process using a collimated deposition.

27. The system of claim 1, wherein said pillars is formed using a step comprising a method selected from nanoimprint or photolithography, or direct embossing.

28. The system of claim 1, wherein said reader comprises a light detector.

29. The system of claim 1, wherein said metallic disc comprises a layer of a metal selected from the group consisting of gold, silver, copper, aluminum, or alloys, or any material that generates plasmons, or combinations thereof.

30. The system of claim 1, wherein said light signal has a wavelength in the range of 100 nm to 20,000 nm.

* * * * *

UNITED STATES PATENT AND TRADEMARK OFFICE
CERTIFICATE OF CORRECTION

PATENT NO. : 10,234,394 B2
APPLICATION NO. : 14/668750
DATED : March 19, 2019
INVENTOR(S) : Stephen Y. Chou et al.

Page 1 of 1

It is certified that error appears in the above-identified patent and that said Letters Patent is hereby corrected as shown below:

In the Specification

In Column 1, Lines 20-24: Please delete the paragraph starting with "This invention" ending with "in this invention." and replace it with the following paragraph:

--This invention was made with government support under Grant No. FA9550-08-1-0222 awarded by the United States Air Force, Office of Scientific Research (AFOSR). The government has certain rights in the invention.--

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*